(12) United States Patent
Kelleher-Andersson et al.

(10) Patent No.: US 7,560,553 B1
(45) Date of Patent: Jul. 14, 2009

(54) USE OF FUSE NICOTINAMIDES TO PROMOTE NEUROGENESIS

(75) Inventors: Judith Kelleher-Andersson, Columbia, MD (US); Karl K. Johe, Potomac, MD (US)

(73) Assignee: Neuralstem, Inc., Rockville, MD (US)

( * ) Notice: Subject to any disclaimer, the term of this patent is extended or adjusted under 35 U.S.C. 154(b) by 0 days.

(21) Appl. No.: 12/049,922

(22) Filed: Mar. 17, 2008

Related U.S. Application Data

(62) Division of application No. 10/914,460, filed on Aug. 9, 2004, now abandoned.

(60) Provisional application No. 60/493,674, filed on Aug. 8, 2003.

(51) Int. Cl.
C07D 401/00 (2006.01)
C07D 213/44 (2006.01)
A61K 31/497 (2006.01)
A61K 31/44 (2006.01)

(52) U.S. Cl. .................. 544/365; 546/262; 514/253.01; 514/332

(58) Field of Classification Search .................. 544/360, 544/365; 546/262; 514/253.01, 332
See application file for complete search history.

(56) References Cited

U.S. PATENT DOCUMENTS

| | | | |
|---|---|---|---|
| 4,753,635 | A | 6/1988 | Sagen et al. |
| 4,980,174 | A | 12/1990 | Sagen et al. |
| 5,082,670 | A | 1/1992 | Gage |
| 5,166,065 | A | 11/1992 | Williams et al. |
| 5,175,103 | A | 12/1992 | Lee et al. |
| 5,411,883 | A | 5/1995 | Boss et al. |
| 5,580,777 | A | 12/1996 | Bernard et al. |
| 5,589,376 | A | 12/1996 | Anderson et al. |
| 5,612,211 | A | 3/1997 | Wilson et al. |
| 5,672,499 | A | 9/1997 | Anderson et al. |
| 5,693,482 | A | 12/1997 | Anderson et al. |
| 5,750,376 | A | 5/1998 | Weiss et al. |
| 5,753,505 | A | 5/1998 | Luskin |
| 5,753,506 | A | 5/1998 | Johe |
| 5,770,414 | A | 6/1998 | Gage et al. |
| 5,824,489 | A | 10/1998 | Anderson et al. |
| 5,849,553 | A | 12/1998 | Anderson et al. |
| 5,851,832 | A | 12/1998 | Weiss et al. |
| 5,928,947 | A | 7/1999 | Anderson et al. |
| 6,040,180 | A | 3/2000 | Johe |
| 6,071,889 | A | 6/2000 | Weiss et al. |
| 6,284,539 | B1 | 9/2001 | Bowen et al. |
| 6,331,553 | B1 * | 12/2001 | Esaki et al. .................. 514/352 |
| 6,369,053 | B1 | 4/2002 | Yuan et al. |
| 6,497,872 | B1 | 12/2002 | Weiss et al. |
| 6,531,464 | B1 | 3/2003 | Jagtap et al. |
| 6,699,871 | B2 | 3/2004 | Edmondson et al. |
| 7,101,709 | B2 | 9/2006 | Weiss et al. |
| 2002/0107273 | A1 | 8/2002 | Nakao et al. |
| 2003/0059369 | A1 | 3/2003 | Kung et al. |
| 2004/0185429 | A1 | 9/2004 | Kelleher-Andersson et al. |

FOREIGN PATENT DOCUMENTS

| | | |
|---|---|---|
| EP | 0 233 838 | 8/1987 |
| WO | WO 89/03872 | 5/1989 |
| WO | WO 90/06757 | 6/1990 |
| WO | WO 91/02003 | 2/1991 |
| WO | WO 91/09936 | 7/1991 |
| WO | WO 91/17242 | 11/1991 |
| WO | WO 93/01275 | 1/1993 |
| WO | WO 93/09802 | 5/1993 |
| WO | WO 94/02593 | 2/1994 |
| WO | WO 94/03199 | 2/1994 |
| WO | WO 94/04675 | 3/1994 |
| WO | WO 94/10292 | 5/1994 |
| WO | WO 95/13364 | 5/1995 |
| WO | WO 96/09543 | 3/1996 |
| WO | WO 96/15226 | 5/1996 |
| WO | WO 98/48001 | 10/1998 |
| WO | WO 99/01159 | 1/1999 |
| WO | WO 99/11758 | 3/1999 |

OTHER PUBLICATIONS

Almazan et al., "Epidermal Growth and Bovine Growth Hormone Stimulate Differentiation and Myelination of Brain Cell Aggregates in Culture," Developmental Brain Research, 21:257-264 (1985).
Almazan et al., "Triiodothyronine Stimulation of Oligodendroglial Differentiation and Myelination," Dev. Neurosci., vol. 7, pp. 45-54, 1985.
Anchan et al., "EGF and TGF- alpha. Stimulate Retinal Neuroepithelial Cell Proliferation in Vitro," Neuron, 6(6):923-936 (1991).
Arsenijevic Y. et al, "Isolation of multipotent neural precursors residing in the cortex of the adult human brain," Experimental Neurology, vol. 170, pp. 48-62, 2001.
Avellana-Adalid, V. et al., "Expansion of Rat Oligodendrocyte Progenitors into Proliferative "Oligospheres" that Retain Differentiation Potential," Journal of neuroscience Research, vol. 45, pp. 558-570, 1996, http://www3.interscience.wiley.com/cgi-bin/abstract/67559/ABSTRACT.
Baetge, E.E., Ann. N.Y. Acad. Sci. 695, 285 (1993).
Barlett, P.F. et al., "Immortalization of mouse neural precursor cells by the c-myc oncogene," Neurobiology, vol. 85, pp. 3255-3259, 1998.
Bartlett, P.F. et al., Clin. Exp. Pharm. Physiol. 22, 559-562 (1995).
Behl C., "Apoptosis and Alzheimer's disease," Journal of Neural transmission, vol. 107, pp. 1325-1344, 2000.
Bernard, O. et al., "Role of the c-myc and the N-myc Proto-Oncogenes in the Immortalization of Neural Precursors," Journal of Neuroscience Research, vol. 24, pp. 9-20, 1989.

(Continued)

*Primary Examiner*—Janet L Andres
*Assistant Examiner*—John Mabry
(74) *Attorney, Agent, or Firm*—Morrison & Foerster LLP

(57) ABSTRACT

The present invention provides a group of compounds found to increase the number of neurons derived from stem cells for use as a therapeutic agent in neurological conditions or diseases. In one embodiment of the present invention, the compounds are used to detect the mechanism by which the number of neurons is increased.

7 Claims, 17 Drawing Sheets

OTHER PUBLICATIONS

Birren, S.J. et al., "A v-myc-Immortalized Sympathoadrenal Progenitor Cell Line in Which Neuronal Differentiation Is Initiated by FGF but Not NGF," Neuron, vol. 4, pp. 189-201, 1990.

Bredesen, D.E. et al., "Neural Transplantation Using Temperature-Sensitive Immortalized Neural Cells: A Preliminary Report," Annals of Neurology, vol. 27, pp. 205-207, 1990.

Bremner, J. D. et al., "Hippocampal volume reduction in major depression," Am. J. Psychiatry, vol. 157, pp. 115-117, 2000.

Brezun, J. et al., "Depletion in serotonin decreases neurogenesis in the dentate gyrus and the subventricular zone of adult rats," Neuroscience, vol. 89, pp. 999-1002, 1999.

Broe, M. et al., "Relationship between DNA fragmentation, morphological changes and neuronal loss in Alzheimer's disease and dementia with Lewy bodies," Acta Neuropathol, vol. 101, pp. 616-624, 2001.

Brustle et al. (1999) Science 285,754.

Calof A L. et al., "Analysis of neurogenesis in a mammalian neuroepithelium: proliferation and differentiation of an olfactory neuron precursor in vitro," Neuron, vol. 3, pp. 115-127, 1999.

Cambray-Deakin, M.A. The expression of excitatory amino acid binding sites during neuritogenesis in the developing rat cerebellum. Ref. No. 78577. Biol Abstr vol. 90, 1990.

Cameron H A. et al., "Regulation of neurogenesis by growth factors and neurotransmitters," Journal of Neurobiology, vol. 36, pp. 287-306, 1998.

Cao Q. et al., "Stem Cell Repair of Central Nervous System Injury," Journal of Neuroscience Research, vol. 68, pp. 501-510, 2002.

Carpenter et al, 1997, Exp. Neurol., 148: 187-204.

Carpenter et al. (1939) Erp. Neurol. 158,265.

Carpenter; Reexamination Control No. 90/008862 for Patent No. 6,103,530, Cultures of Human CNS Neural Stem Cells.

Castillo et al., Genomics 41:250-257 (1997).

Castillo et al., Mol. Cell. Neurosci. 11:36-46 (1998).

Cattaneo, E. et al., "Proliferation and differentiation of neuronal stem cells regulated by nerve growth factor," Letters To Nature, vol. 347, pp. 762-765, 1990.

Cepko, C.L., "Immortalization of Neural Cells Via Retrovirus-Mediated Oncogene Transduction," Annu. Rev. Neurosci., vol. 12, pp. 47-65, 1989.

Chabot, P. Transient expression of an intermediate filament-associated protein (IFAPa-400) during in vivo and in vitro differentiation of chick embryonic cells derived from neuroectoderm. Ref. No. 78577. Biol Abstr vol. 90, 1990.

Conover et al., Ciliary Neurotrophic Factor Maintains the Pluripotentiality of Embryonic Stem Cells, Development 119, pp. 559-565 (1993).

Coon H G. et al., "Cell cultures of neuroblasts from rat olfactory epithelium that show odorant responses," Neurobiology, vol. 86, pp. 1703-1707, 1989.

Coppell, A. L. et al., "Bi-phasic change in BDNF gene expression following antidepressant drug treatment," Neuropharmacaology, vol. 44, pp. 903-910, 2003.

Czeh, B. et al., "Stress-induced changes in cerebral metabolites, hippocampal volume, and cell proliferation are prevented by antidepressant treatment with tianepine," PNAS, vol. 98, pp. 12796-12801, 2001.

Davis, A.A. & Temple, S., Nature 372, 263-266 (1994).

DiCicco-Bloom, E. et al., "Neuroblast Mitosis in Dissociated Culture: Regulation and Relationship to Differentiation," The Journal of Cell Biology, vol. 110, pp. 2073-2086, 1990.

Drago, J. et al., :Fibroblast Growth Factor-Mediated Prolifereation of Central Nervous System Precursors Depends on Endogenous Production of Insulin-like Growth Factor I, Neurobiology, vol. 88, pp. 2199-2203, 1991.

Drago, J. et al., "A Method for the Isolation of Purified Murine Neuroepithelial Cells From the Developing Mouse Brain," Journal of Neuroscience Methods, vol. 37, pp. 251-256, 1991.

Drago, J. et al., "Basic Fibroblast Growth Factor Upregulates Steady-State Levels of Laminin B1 and B2 Chain mRNA in Cultured Neuroepithelial Cells," Experimental Cell Research, vol. 196, pp. 246-254, 1991.

Drago, J. et al., "Laminin through its Long Arm E8 Fragment Promotes the Proliferation and Differentiation of Murine Neuroepithelial Cells in Vitro," Experimental Cell Research, vol. 192, pp. 256-265, 1991.

DZZZSa, C. et al., "Antidepressants and neuroplasticity," Bipolar Disorders, vol. 4, pp. 183-194, 2002.

Dutton, G.R. "Isolation, Culture, and Use of Viable Central nervous System Perikarya," Methods in Neuroscience, vol. 2, pp. 87-102, 1990.

Ehrlich, M.E. et al. "DARPP-32 development in the caudate nucleus is independent of afferent input from the substantia nigra," Ref. No. 78577. Biol Abstr vol. 90, 1990.

Eilers et al. (1989) Nature 340, 66.

Eriksson P S. et al., "Neurogenesis in the adult human hippocampus," Nature Medicine, vol. 4, pp. 1313-1317, 1998.

Escary et al., Leukaemia Inhibitory Factor is Necessary for Maintenance of Haematopoietic Stem Cells and Thymocyte Stimulation, Nature, vol. 363, pp. 361-364 (May 27, 1993).

Evrard et al., Immortalization of bipotential and plastic glio-neuronal precursor cells, Proc. Natl. Acad. Sci. USA vol. 98, pp. 3062-3066, Apr. 1990 Developmental Biology.

Falk A. et al., "Amphiregulin is a mitogen for adult neural stem cells," Journal of Neuroscience Research vol. 69, pp. 757-762, 2002.

Feron F. et al., "Stress induces neurogenesis in non-neuronal cell cultures of adult olfactory epithelium" Neuroscience, vol. 88, pp. 571-583, 1999.

Finger S. et al., "Nimodipine and Neural Grafts," Duke Med Cent Lib 34. P2, p. 208, 1991.

Fischer, A.J. et al. "Exogenous Growth Factors Induce the Production of Ganglion Cells at the Retinal Margin," Development, vol. 129, pp. 2283-2291, 2002.

Flax et al. (1998) Nature Biotech. 16, 1033.

Frappaz, D. et al., "Enhancement of Growth of Primary Metastatic Fresh Human Tumors of the Nervous System by Epidermal Growth Factor in Serum-free Short Term Culture," Neurosurgery, vol. 23, pp. 355-359, 1998.

Frederiksen, K. et al., "Immortalization of Precursor Cells for the Mammalian CNS," Neuron, Vol. 1, pp. 439-448, 1988.

Gage, F.H., Ray, J. & Fisher, L.J. Annu. Rev. Neurosci. 18, 159-192 (1995).

Glasky et al., "Update: Central and Peripheral Nervous Systems AIT-082, a novel purine derivative with neuroregenerative properties," Exp. Opin. Invest. Drugs, vol. 6, pp. 1413-1417, 1997.

Godfraind, C. et al., "In Vivo Analysis of Glial Cell Phenotypes During a Viral Demyelinating Disease in Mice," The Journal of Cell Biology, vol. 109, pp. 2405-2416, 1989.

Goldman S A. et al., "In vitro neurogenesis by neuronal precursor cells derived from the adult songbird brain," The Journal of Neuroscience, vol. 12, pp. 2532-2541, 1992.

Gould E. et al., "Inaugural Article: Adult-generated hippocampal and neocortical neurons in macaques have a transient existence," PNAS, vol. 98, pp. 10910-10917, 2001.

Green et nl., Nature 326: 134-139, 1986.

Gritti, A., et al., J. Neurosci. 16, 1091-1100 (1996).

Gu W. et al., "Cortical neurogenesis in adult rats after reversible photothrombotic stroke," Journal of Cerebral Blood Flow and Metabolism, vol. 20, pp. 1166-1173, 2000.

Guentert-Lauber, et al., Responsiveness of Astrocytes in Serum-Free Aggregate Cultures to Epidermal Growth Factor: Dependence on the Cell and the Epidermal Growth Factor Concentration, Dev. Neurosci. 7: pp. 286-295 (1985).

Hall et al, 1992, An Introduction to Molecular Neurobiology, p. 357.

Hata, M. et al., "A decrease in the wet-dog shakes response to the second administration of kainic acid in juvenile rats," Ref. No. 31832, Biol Abstr vol. 92, 1991.

Hauser K F. et al., "Opioids intrinsically inhibit the genesis of mouse cerebellar granule neuron precursors in vito: differential impact of mu and delta receptor activation on proliferation and neurite elongation," European Journal of Neuroscience, vol. 12, pp. 1291-1293, 2000.

Hermanson, M., Olsson, T., Wetermark, B. & Funa K., Exp. Brain Res. 102, 415-422 (1995).

Hollenberg et al., Epidermal Growth Factor: Receptors in Human Fibroblasts and Modulation of Action by Cholera Toxin, Proc. Natl. Acad. Sci. USA vol. 70, No. 10, pp. 2964-2968 (1973).

Honegger, P. et al., "Growth and Differentiation of Aggregating Fetal Brain Cells in a Serum-Free Defined Medium," Nature, vol. 282, pp. 305-308, 1979.

Honkaniemi et al., Mol. Brain Res. 28:157-163 (1995).

Horcholle-Bossavit, G. et al., "Postnatal development of peroneal motoneurons in the kitten," Ref. No. 78577. Biol Abstr vol. 90, 1990.

Hoshimaru et al. (1996) PNAS 93, 1518.

Howland et al., "Focal loss of the glutamate transporter EAAT2 in a transgenic rat model of SOD1 mutant-mediated amyotrophic lateral sclerosis (ALS)," PNAS, vol. 99, pp. 1604-1609, 2002.

Hunter et al., "Growth factor responses of enriched bipotential glial progenitors," Biol. Abstr. 90:7, Abstract No. 78581 (1990).

Ishibashi et al., "Human Neural Stem/Progenitor Cells, Expanded in Long-Term Neurosphere Culture, Promote Fuctional Recovery After Focal Ischemia in Mongolian Gerbils," Journal of Neuroscience Research, vol. 78, pp. 215-223, 2004.

Jelitai M. et al., "Regulated appearance of NMDA Receptor Subunits and Channel Functions Duriing In Vitro Neuronal Differentiation," Journal of Neurobiology, vol. 51, pp. 54-65, 2002.

Jin K. et al., "Stem cell factor stimulates neurogensis in vitro and in vivo." The Journal of Clinical Investigation, vol. 110, pp. 311-319, 2002.

Jin K. et al., "Vascular endothelial growth factor (VEGF) stimulates neurogensis in vitro and in vivo," PNAS, vol. 99. pp. 11946-11950, 2002.

Jones-Villeneuve, et al., "Retinoic Acid Induces Embryonal Carcinoma Cells to Differentiate into Neurons and Glial Cells," The Journal of Cell Biology, vol. 94, pp. 253-262, 1982.

Jung et al. (1998) Eur. J. Neuroscj 10,3246.

Kehl L J. et al., "Neurogenesis in postnatal rat spinal cord: a study in primary culture," Science, vol. 276, pp. 586-589, 1997.

Kempermann, G. et al., "Depressed new neurons-adult hippocampal neurogenesis and a cellular plasticity hypothesis of major depression," Biological Psychiatry, vol. 54, pp. 499-503, 2003.

Kempermann, G. et al., "Genetic determinants of adult hippocampal neurogenesis correlate with acquisition, but not probe trial performance, in the water maze task," European Journal of Neuroscience, vol. 16, pp. 129-136, 2002.

Kershaw, T.R. et al., "Foetal H-2Kb-tsA58 Transgenic Mouse Tissue Develops in a Similar Manner to ISO Geneic Foetal Tissue when Transplanted into Adult Mouse Brain," Duke Med Cent Lib 34, P4, p. 208, 1991.

Kilpatrick et al., "Cloning and Growth of Multipotential Neural Precursors: Requirements for Proliferation and Differentiation," vol. 10, pp. 255-265, 1993.

Kilpatrick, T.J., and Bartlett, P.F., J. Neurosci. 15, 3653-3661 (1995).

Kilpatrick, T.J., Richards, L.J., and Bartlett, P.F., Mol. Cell. Neurosci. 6, 2-15 (1995).

Kitani, H. et al., "Isolation and Characterization of Mouse Neural Precursor Cells in Primary Culture," In Vitro Cell. Dev. Biol., vol. 27A, pp. 615-624, 1991.

Kuhn, H. G. et al., "Neurogenesis in the dentate gyrus of the adult rat age-related decrease of neuronal progeneitor proliferation," The Journal of Neuroscience, vol. 16, pp. 2027-2033, 1996.

Kumar et al., The EMBO Journa 5: 2231-2236, 1986.

Law et al., Gene Expr. 4:77-84 (1994).

Lee et al. (1999) Oncogene 18,2997.

Lee, A. L. et al., "Stress and depression: possible links to neurons death in the hippocampus, " Bipolar Disorders, vol. 4, pp. 117-128, 2002.

Lee, J. et al., "Dietary restriction increases the number of newly generated neural cells, and induces BDNF expression, in the dentate gyrus of rats," Journal of Molecular Neuroscience, vol. 15, pp. 99-108, 2001.

Lichtenwalner, R. J. et al., "Intracerebroventricular infusion of insulin-like growth factor-1 ameliorates the age-related decline in hippocampal neurogenesis," Neuroscience, vol. 107, pp. 603-613, 2001.

Ling et al., Exp. Neurol. 149:411-423 (1998).

Lois et al (1993) Proc. Nat'l Acad. Sci. 90: 2074-2077.

Lovejoy, D.A. et al., "Primary structure of two forms of gonadotropin-releasing hormone from brains of the American alligator," Ref. No. 31832, Biol Abstr Vol. 92, 1991.

Lucassen, P. J. et al., "Hippocampal apoptosis in major depression is a minor event and absent from subareas at risk for glucocorticoid overexposure," American Journal of Pathology, vol. 158, pp. 453-468, 2001.

Lyman, W.D. et al., "Human Fetal Central Nervous System Organotypic Cultures," Developmental Brain Research, vol. 60, pp. 155-160, 1991.

Ma W. et al., "Acetylcholine stimulates cortical precursor cell proliferation in vitro via muscarinic receptor activation and MAP kinase phosphorylation," European Journal of Neuroscience, vol. 12, pp. 1227-1240, 2000.

Madsen T M. et al., "Increased neurogenesis in a model of electroconvulsive therapy," Biological Psychiatry, vol. 47, pp. 1043-1049, 2000.

Mages et al., Mol. Endocrinol. 8:1583-1591 (1994).

Malberg, J. E. et al., "Chronic antidepressant treatment increases neurogenesis in adult rat hippocampus," The Journal Of Neuroscience, vol. 20, pp. 9104-9110, 2000.

Marin N. et al., $\beta$.-amyloid-induced activation of caspase-3 in primary cultures of rat neurons, Mechanisms of Ageing and Development, vol. 119, pp. 63-67, 2000.

Masters et al., "Insulin-like growth factor I (IGF-I) receptors and IGF-I action in oligodendrocytes from rat brains," Biol. Abstr. 93.3, Abstract No. 31828 (1992).

Mauerhoff, T. et al., Differential Expression and Regulation of Major Histocompatibility Complex (MHC) Products in Neural and Glial Cells of the Human Fetal Brain, Journal of Neuroimmunology, vol. 18, pp. 271-289, 1988.

Mayo W. et al., "Pregnenolone sulfate and aging of cognitive functions: behavioral, neurochemical, and morphological investigations," Hormones and Behavior, vol. 40, pp. 215-217, 2001.

McCarthy, M. et al., "Infection of Human Neural Cell Aggregate Cultures with a Clinical Isolate of Cytomegalovirus," Journal of Neuropathology and Experimental Neurology, vol. 50, pp. 441-450, 1991.

McKay, R. et al., "Mechanisms Regulating Cell number and Type in the Mammalian Central Nervous System," Cold Spring Harbor Symposia on Quantitative Biology, vol. LV, pp. 291-301, 1990.

Mervaala, E. et al., "Quantitative MRI of the hippocampus and amygdala in severe depression," Psychological Medicine, vol. 30, pp. 117-125, 2000.

Monnet-Tschudi et al., Influence of Epidermal Growth Factor on the Maturation of Fetal Rat Brain Cells in Aggregate Culture, Dev. Neurosci. 11: pp. 30-40 (1989).

Morrison, R.S. et al., "Trophic Stimulation of Cultured Neurons from Neonatal Rat Brain by Epidermal Growth Factor," Science, vol. 238, pp. 72-75, 1987.

Murphy, M. et al., "Fibroblast Growth Factor Stimulates the Proliferation and Differentiation of Neural Precursor Cells In Vitro," Journal of Neuroscience Research, vol. 25, pp. 463-475, 1990.

Murrell W. et al., "Neurogenesis in adult human," NeuroReport, vol. 7, pp. 1189-1194, 1996.

Mytilineou, C. et al., "Epidermal Growth Factor-Induced Survivial and Proliferation of Neuronal Precursor Cells from Embryonic Rat Mesencephalon,"Neuroscience Letters, vol. 135, pp. 62-66, 1992.

Nakafuku et al., "Establishment and Characterization of a Multipotential Neural Cell Line That Can Conditionally Generate Neurons, Astrocytes, and Oligodendrocytes In Vitro," Journal of Neuroscience Research, vol. 41, pp. 153-168, 1995.

Nakagawa, S. et al., "Regulation of neurogenesis in adult mouse hippocampus by cAMP and the cAMP reponse element-binding protein," The Journal Of Neuroscience, vol. 22, pp. 3673-3682, 2002.

Nestler, E.J. et al., "Neurobiology of Depression," Neuron, vol. 34, pp. 13-25, 2002.

Nibuya,, M. et al., "Chronic antidepressant administration increases the expression of cAMP response element binding protein (CREB) in rat hippocampus." The Journal of Neuroscience, vol. 16, pp. 2365-2372, 1996.

Nielsen, F.C. et al., "Receptor Binding, Endocytosis. and Mitogenesis of Insulin-Like Growth Factors I and III in Fetal Rat Brain Neurons," Journal of Neurochemistry, vol. 56, pp. 12-21, 1991.
Ohkura et al., Biochim. Biophys. Acta 1308:205-214 (1996).
Okabe et al., J. Immunol. 154:3871-3879 (1995).
Okano et al., "Neural stem cells and regeneration of injured spinal cord," Kidney International, vol. 68, pp. 1927-1931, 2005.
Okano, H., "Neural stem cells: progression of basic research and perspective for clinical application," Keio Journal of Medicine, vol. 51, pp. 115-128, 2002.
Palmer T D. et al., "Ffibroblast growth factor-2 activates a latent neurogenic program in neural stem cells from diverse regions of the adulf CNS," The Journal of Neuroscience, vol. 19, pp. 8487-8497, 1999.
Park K. et al., "Global gene and cell replacement strategies via stem cells," Gene Therapy, vol. 9, pp. 613-624, 2002.
Pena de Oritz et al., Mol. Brain Res. 38:1-13 (1996).
Perrone-Capano et al., Bioessays 18:817-824 (1996).
Peterson D. A et al., "Trophic factor therapy for neuronal death," Alzheimer Disease, $2^{nd}$ Edition, Chapter 25, pp. 373-388, 1999.
Pham, K. et al., "Repeated restraint stress suppresses neurogenesis and induces biphasic PSA-NCAM expression in the adult dentate gurus," Eurpean Journal of Neuroscience, vol. 17, pp. 879-886, 2003.
Piescindek, P. et al., "Neurogenesis of the amygdaloid complex in the rhesus monkey," Society for Neuroscience Abstracts, vol. 16, p. 1147, 1990.
Pincus D W. et al., "In vitro neurogenesis by adult human epileptic temporal neocortex," Clinical Neurosurgery, Chapter 2, pp. 17-25.
Pollerberg et al., "Generation of Cell Lines From Embryonic Quail Retina Capable of Mature Neuronal Differentiation," Journal of Neuroscience Research, vol. 41, pp. 427-442, 1995.
Pucilowski, O. et al., Decreased hyperthermic effect of MK801 in selectively bred hypercholinergic rats, Ref. No. 31832, Biol Abstr vol. 92, 1991.
Puliam, L. et al., "A Normal Human Brain Cell Aggregate Model for Neurobiological Studies," Journal of Neuroscience Research, vol. 21, pp. 521-230, 1988.
Qu, T. et al., "Human neural stem cells improve cognitive function of aged brain," NeuroReport, vol. 12, pp. 1127-1132, 2001.
Raina, A K. et al., "Abortive apoptosis in Alzheimer's disease," Acta Neuropathol, vol. 101, pp. 305-310, 2001.
Rao et el. (1997) J. Neurobiol. 32,722.
Rathbone M P,et al., "Trophic effects of purines in neurons and glial cells," Progress in Neurobiology, vol. 59, pp. 663-690, 1999.
Ray, J. and Gage, F. H., J. Neurosci. 14, 3548-3564 (1994).
Ray, J. Peterson, D., Schinstine, M. & Gage, F. Proc. Natl. Acad. Sci. USA 90,3602-3606 (1993); Genetics 9,265-260 (1995).
Reichmann et nl. (1992) Cell 71,1103.
Renoncourt et nl. (1998) Mechanisms of Development 78,185.
Resnick et al., Long-term Proliferation of Mouse Primordial Germ Cells in Culture, Nature, vol. 359, pp. 550-551 (Oct. 8, 1992).
Rettig, W.J. et al., "Cell Type-specific Control of Human Neuronectin Secretion by Polypeptide mediators and Phorbol Ester," The Journal of Histochemistry and Cytochemistry, vol. 37, pp. 1777-1786, 1989.
Rettig, W.J. et al., "Stimulation of Human Neuronectin Secretion by Brain-Derived Growth Factors," Brain Research, vol. 487, pp. 171-177, 1989.
Reynolds, B.A. et al., "A Multipotent EFG-Responsive Striatal Embryonic Progenitor Cell Produces Neuron and Astrocytes," The Journal of Neuroscience, vol. 12, pp. 4565-4574, 1992.
Reynolds, B.A. et al., "A Non-Transformed, Growth Factor Dependent Stem Cell Line Derived From the Embryonic Mouse CNS Produces Neurons, Astrocytes and Oligodendrocytes," Duke Med Cent Lib 34.P3, p. 208, 1991.
Reynolds, B.A. et al., "EGF- and TFGα-responsive striatal embryonic progenitor cells produce both neurons and astocytes," Society for Neuroscience Abstracts, vol. 16, p. 1147, 1990.
Reynolds, B.A. et al., "Generation of Neurons and Astocytes from Isolated Cells of the Adult Mammalian Central Nervous System," Science, vol. 255, pp. 1707-1709, 1992.
Righi et el. (1935) J. Neurochem. 64, 121.
Rind H. et al., "Synaptic Targeting of Retrogradely Transported Trophic Factors in Mononeurons: Comparison of Glial Cell Line-Derived Neurotrophic Factor, Brain-Derived Neurotrophic Factor, and Carpiotrophin-1 with Tetanus Toxin," The Journal of Neuroscience, vol. 25, pp. 539- 549, 2005.
Romand, R. et al., "Development of tonotopy oin the inferior colliculus: 1. Electrophysiological mapping in house mice," Ref. No. 78577. Biol Abstr vol. 90, 1990.
Roth, K. A., "Caspases, apoptosis, and Alzheimer disease: causation, correlation, and confusion," Journal of Neuropathology and Experimental Neurology, vol. 60, pp. 829-838, 2001.
Rothstein J.D. et al., "Decreased Glutamate Transport by the Brain and Spinal Cord in Amyotrophic Lateral Sclerosis," The New England Journal of Medicine, vol. 326, pp. 1464-1468, 1992.
Roy N S, et al., "In vitro neurogenesis by progenitor cells isolated from the adult human hippocampus," Nature Medicine, vol. 6, pp. 271-277, 2000.
Rozental R. et al., "Differentiation of hippocampal progenitor cells in vitro: temporal expression of intercellular coupling and voltage- and lignad-gated responses," Developmental Biology, vol. 167, pp. 350-362, 1995.
Rudland et al., Growth Control in Cultured Mouse Fibroblasts: Induction of the Pleiotypic and Mitogenic Responses by a Purified Growth Factor, Proc. Natl. Acad. Sci, USA vol. 71, No. 7, pp. 2600-2604 (1974).
Rutka, J.T. et al., "Characterization of Fetal Human Brain Cultures," Dev. Neurosci., vol. 9, pp. 154-173, 1987.
Ryder et al. (1990) J. Neurobiol. 21,356.
Sabate, O., Horellou, P., Vigne, E., Colin, P., Perricaudet, M., Buc-Caron, M.-H. & Mallet, J., Nature Genetics 9, 256-260 (1995).
Sah et al. (1997) Nature Biotech. 15,574.
Sales, N. et al., Neutral endopeptidase 24.11 in rat peripheral tissues: comparative localization bby "ex vivo" and "in vitroautoradiography," Ref. No. 31832, Biol Abstr vol. 92, 1991.
Saneto, R.P. et al., "Insulin/Insulin-Like Growth Factor I and Other Epigenetic Modulators of Myelin Basic Protein Expression in Isolated Oligodendrocyte Progenitor Cells," Journal of Neuroscience Research, Vo. 21, pp. 210-219, 1988.
Santarelli, L. et al., "Requirement of hippocampal neurogenesis for the behavioral effects of antidepressants," Science, vol. 301, pp. 805-809, 2003.
Sato, H. et al., "Somatostafin receptors in the senescent rat brain: A quantitative autoradiographic study," Ref. No. 31832, Biol Abstr vol. 92, 1991.
Satoh M. et al., "Promotion of neurogenesis in mouse olfactory neuronal progenitor cells by leukemia inhibitory factor in vitro," Neuroscience Letters, vol. 225, pp. 165-168, 1997.
Saucedo-Cardenas et al., Gene 187:135-139 (1997).
Saucedo-Cardenas et al., Proc. Natl. Acad. Sci. USA 95:4013-4018 (1998).
Scearce et al., J. Biol. Chem. 268:8855-8861 (1993).
Schapira, Baillieres Clin. Neurol. 6:15-36 (1997).
Scott B W. et al., "Neurogenesis in the dentate gyrus of the rat following electroconvulsive shock seizures," Experimental Neurology, vol. 165, pp. 231-236, 2000.
Seaberg R M. et al., "Adult rodent neurogenic regions: the ventricular subependyma contains neural stem cells, but the dentate gyrus contains restricted progenitors," The Journal of Neuroscience, vol. 22, pp. 1784-1793, 2002.
Seigel, G.M. et al., "Differentiation of oncogenically altered chick neuroretinal cells by succinylated concanavalin A," Society for Neuroscience Abstracts, vol. 16, pp. 1147, 1990.
Selvakurnarun et ul. (1993) Blood 81,2257.
Shingo T. et al., "Erythropoietin regulates the in vitro and in vivo production of neuronal progenitors by mammalian forebrain neural stem cells," The Journal of Neuroscience, vol. 21, pp. 9733-9743, 2001.
Shirayama, Y. et al., "Brain-derived neurotrophic factor produces antidepressant effects in behavioral models of depression," The Journal of Neuroscience, Vol. 22, pp. 3251-3261, 2002.
Shors T J. et al., "Neurogenesis in the adult is involved in the formation of trace memories," Nature, vol. 410, pp. 372-376, 2001.
Shou J. et al., "BMPs inhibit neurogenesis by a mechanism involving degradation of a transcription factor," Nature Neuroscience, vol. 2, pp. 339-345, 1999.

Silani, V. et al., "Human Neuronal Cells In Culture: From Concepts to Basic Methodology," Boll. 1st. Sieroter. Mila., vol. 69, pp. 309-313, 1990.

Sorensen, K.A. et al., "Postembryonic neurogenesis in the Brain of Manduca Sexta," Society for Neuroscience Abstracts, vol. 16, p. 1147, 1990.

Stemple et al, 1997, Neuron, 18:1-4.

Sternfeld, M.D. et al., "Cultured Human Retinal Pigment Epithelial Cells Express Basic Fibroblast Growth Factor and its Receptor," Current Eye Research, vol. 8, pp. 1029-1037, 1989.

Stewart, J.S. et al., "Olfactory bulb and sensory epithelium in goldfish: Morphological alterations accompanying growth," Ref. No. 78577. Biol Abstr vol. 90, 1990.

Stone et al., Molecular and Cellular Biology 7: 1697-1709, 1987.

Svendsen, C.N. & Rosser, A.E., Trends in Neuroscience 18, 465-466 (1995).

Svendsen, C.N., Fawcett, J.W., Bentlage, C. & Dunnett, S.B., Exp. Brain Res. 102, 407-44114 (1995).

Takahashi J. et al., "Retinoic acid and neurotrophins collaborate to regulate neurogenesis in adult-derived neural stem cell cultures," J Neurobiol, vol. 38, pp. 65-81, 1999.

Takahashi, T. et al., "Cell cycle kinetics of the E14 murine cerebral ventricular zone: estimates based upon S-Phase labeling with BUdR," Society for Neuroscience Abstrats, vol. 16, p. 1147, 1990.

Taupin P, et al., "FGF-2-responsive neural stem cell proliferation requires CCg, a novel autocrine/paracrine cofactor," Neuron, vol. 28, pp. 385-397, 2000.

Taylor, M. et a., "Induction of Differentiation of Rat Retinal, Germinal, Neuroepithelial Cells by dbcAMP," Journal of Neurobiology, vol. 21, pp. 470-481, 1990.

Temple, S., "Division and Differentiation of Isolated CNS Blast Cells in Microculture," Nature, vol. 340, pp. 471-473-1989.

Tenot, M. et al., Epidermal Growth Factor Enhances the Expression of an Edogenous Lectin in Aggregating Fetal Brain Cell Cultures, Journal of Neurochemistry, vol. 53, pp. 1435-1441, 1989.

Torelli, S. et al., "Human Fetal Brain Cultures: A Model to Study Neural Proliferation, Differentiation and Immunocompetence," Adv. Exp. Med. Biol, vol. 296, pp. 121-134, 1991.

Torres, R.A. et al., "Alteration of Neuronal Regulation of Astrocytoma Proliferation by Insertional Mutagenesis," Society for Neuroscience Abstracts, vol. 16, p. 1147, 1990.

Turner M.R. et al., "Abnormal cortical excitability in sporadic but not homozygous D90A SODI ALS," J Neurol Neurosurg Psychiatry, vol. 76, pp. 1279-1285, 2005.

Unsicker et al., Ciba Found Symp. 196:70-84 (1996).

Van Praag et al., "Running enhances neurogenesis, learning, and long-term potentiation in mice," PNAS, vol. 96, pp. 13427-13431, 1999.

Van Praag et al., "Running increases cell proliferation and neurogenesis in the adult mouse dentate gyrus," Nature Neuroscience, vol. 2, pp. 266-270, 1999.

Vescovi et al. (1999) Exp. Neurol. 156, 71.

Vescovi, A.L., Reynolds, B.A. Fraser, D.D., and Weiss, S., Neuron 11, 951-966 (1993).

Vicario-Abejon, C., Johe, K., Hazel, T., Collazo, D. & McKay, R., Neuron 15, 105-114 (1995).

Villa, A. et al., "Intracellular calcium ion stores in chicken purkinje neurons; Differential distribution of the low affinity-high capacity calcium binding protein, calsequestion, of calcium ATPase and of the ER luminal protein," Bip. Ref. No. 31832, Biol Abstr vol. 92, 1991.

Von Frijtag, J. C. et al., "Chronic imipramine treatment partially reverses the long-term changes of hipocampal synaptic plasticity in socially stressed rats," Neuroscience Letters, vol. 309, pp. 153-156, 2001.

Von Visger, Experimental Neurolgoy 128: 34-40, 1994.

Vu, E.T. et al., "Evidence for a Computational Distinction Between Proximal and Distal Neuronal Inhibition," Science, vol. 255, pp. 1710-1712, 1992.

Wagner et al, 1999, Nat. Biotech., 17: 653-659.

Wainer, B.H. et al., "In vitro cell cultures as model of the basal forebrain," Adv Exp Med Biol., vol. 295, pp. 415-437, 1991.

Wang et al. (1994) PNAS 91, 8180.

Wang et al., "Induction of dopaminergic neurono phenotype in the midbrain by Sonic hedgehog protein," Nature Medicine, vol. 1, pp. 1184-1188, 1995.

Watanabe, R.T. et al., "Rod Photoreceptor development in vitro: intrinsic properties of proliferating neuroepithlial cells change as development proceeds in the rat retina," NeuralCulture, Abstract, 1990.

Watt et al., Nnture 303: 725-728, 1983.

Weiss et al., "Multipotent CNS Stem Cells Are Present in the Adult Mammalian Spinal Cord and Ventricular Neuroaxis," The Journal of Neuroscience, vol. 16, pp. 7599-7609, 1996.

Weiss, et al., Reexamination Control No. 90/008366 for Patent No. 7,101,709, Methods of Screening Biological Agents.

Weiss, et al.; Reexamination Control No. 90/008366 for Patent No. 7,101,709, Methods of Screening Biological Agents; Office Action in Ex Parte Reexamination.

Weiss, et al.; Reexamination Control No. 90/008367 for Patent No. 6,294,346, Use of Multipotent Neural Stem Cells and Their Progeny for the Screening of Drugs and Other Biological Agents.

Weiss, et al.; Reexamination Control No. 90/008367 for Patent No. 6,294,346, Use of Multipotent Neural Stem Cells and Their Progeny for the Screening of Drugs and Other Biological Agents; Office Action in Ex Parte Reexamination.

Weiss, et al.; Reexamination Control No. 90/008580 for Patent No. 5,851,832, In Vitro Growth and Proliferation of Multipotent Neural Stem Cells and Their Progeny.

Weiss, et al.; Reexamination Control No. 90/008580 for Patent No. 5,851,832, In Vitro Growth and Proliferation of Multipotent Neural Stem Cells and Their Progeny; Office Action in Ex Parte Reexamination.

Weiss, et al.; Reexamination Control No. 90/008581 for Patent No. 6,497,872, Neural Transplantation Using Proliferated Multipotent Neural Stem Calls and Their Progeny.

Weiss, et al.; Reexamination Control No. 90/008581 for Patent No. 6,497,872, Neural Transplantation Using Proliferated Multipotent Neural Stem Calls and Their Progeny; Office Action in Ex Parte Reexamination.

Wohl C A, et al., "Retinoic acid enhances neuronal proliferation and astroglial differentiation in cultures of CNS stem cell-derived precursors," J Neurobiol, vol. 37, pp. 281-290, 1998.

Wolswijk et al., "Identification of an adult-specific glial progenitor cell" Development, 105:387-400 (1989).

Xing et al., "Rat nurrl is prominently expressed in perirhinal cortex, and differentially induced in the hippocampal dentate gyrus by electroconvulsive vs. kindled seizures," Molecular Brain Research, vol. 47, pp. 251-261, 1997.

Xu et al., "The extremem C terminus of progesterone receptor contains a transcriptional repressor domain that functions through a putative corepressor," Proc. Natl. Acad. Sci., vol. 93, pp. 12195-12199, 1996.

Xu, L. et al., "Glucocorticoid receptor and protein/RNA synthesis-dependent mechanisms underlie the control of synaptic plasticity by stress," PNAS, vol. 95, pp. 3204-3208, 1998.

Yamada et al. (1999) Neurosci. Letters 264, 165.

Yan J. et al., "Differentiation and Tropic/Trophic Effects of Exogenous Neural Precursors in the Adult Spinal Cord," vol. 480, pp. 101-114, 2004.

Yan, J. et al., "Grafted Human Neural Stem (NS) Cells Differentiate Into Neurons, Migrate Long Distance and Project Axons in Spinal Cord and the Roots of Adult Rats," Program No. 150.19, Abstract Viewer/Ininerary Planner. Society for Neuroscience, 2003.

Ye et al., Cell 93:755-766 (1998).

Yoshimoto, Y. et al, "The Effect of Cool Storage on the Survivability of Intraventricular Rat Fetal Ventral Mesencephalic Graft," Duke Med Cent Lib 34.P1, p. 208, 1991.

Zetterstrom et al., "Cellular expression of the immediate early transcription faxtors Nurr 1 and NGFI-B suggests a gene regulatory role in several brain regions including the nigrostriatal dopamine system," Molecular Brain Research, vol. 41, pp. 111-120, 1996.

Zetterstrom et al., Science 276:248-250 (1997).

Zhang, R. et al, "A nitric oxide donor induces neurogenesis and reduces functional deficits after stroke in rats," Ann. Neurol., vol. 50, pp. 602-611, 2001.

* cited by examiner

USE OF FUSE NICOTINAMIDES TO PROMOTE NEUROGENESIS

PRIORITY CLAIM

The present application is a divisional of and claims priority to and the benefit of U.S. patent application Ser. No. 10/914,460, filed Aug. 9, 2004, which claims priority to and the benefit of U.S. Provisional Application No. 60/493,674 filed Aug. 8, 2003, each of which are incorporated herein in their entirety by reference.

BACKGROUND

1. Field of the Invention

This invention relates to the use of fused imidazoles, aminopyrimidines, nicotinamides, aminomethylphenoxypiperidines and aryloxypiperidines for use as therapeutic agents and analytical reagents. More particularly this invention relates to these agents as therapeutics for prevention and treatment of neurological conditions and diseases in mammals and reagents for detecting neurogenesis and proliferation.

2. Background

According to a long-held doctrine, no significant numbers of neurons are made in the adult mammal to contribute to the function of the adult mammalian nervous system. However, recent data indicate that adult mammalian brains contain neural precursor cells capable of generating new neurons both in normal and in injured conditions. These new neurons have been quantified in live animals by injecting or feeding in drinking water a marker of dividing cells, bromodeoxyuridine (BrdU) and by immunostaining of post-mortem brains with antibodies against BrdU and neuronal markers. An endogenous marker of dividing cells, Ki-67 protein, has also been used instead of BrdU for this purpose. Thus, in healthy, young rodents, approximately 3,000-15,000 new cells per day are estimated to be born in the dentate gyrus of the hippocampus, about 60% of which express early neuron-specific proteins such as doublecortin and type III beta-tubulin. Significant numbers of new cells and new neurons have also been observed in healthy, young primates. In rodents as well as in primates, the location of neurogenic areas in the central nervous system (CNS) is limited to the dentate gyrus of the hippocampus and the subependymal layer of the striatum. In human patients of different ages who have been diagnosed with a tumor of the tongue, a single injection of BrdU has revealed significant number of new cells and new neurons being born in the dentate gyrus and the subependymal layer of the striatum. Thus, adult mammalian brains contain neural stem cells capable of differentiating into neurons, and this process of generating new neurons (neurogenesis) occurs in the mature, adult brain in significant quantities throughout rodents, primates, and human species.

Such significant quantities of new neurons suggest that the new neurons may be important for the normal physiology of the brain, especially the hippocampus. The hippocampus is the main area of neurogenesis in adult rodents and is central for key cognitive functions such as learning and memory where new information is added, edited, stored, and recalled constantly throughout life.

Since the hippocampus is the most potent neurogenic area of the brain, many studies have been undertaken to establish whether neurogenesis may be the cellular mechanism to structurally accommodate the ever-increasing volume of cognitive processing to be handled. Thus, it has been shown that at least some of the newly born neurons, marked by genetic markers, mature to be electrophysiologically active and integrate into the existing neuronal circuitry of the hippocampus. Ablation of the neurogenesis in rats leads to decreased cognitive capabilities in several behavior tests. Thus, the existing data demonstrate that neurogenesis significantly contributes to the normal hippocampal physiology.

For example, most antidepressants are thought to work by increasing the levels of monoamines available for post-synaptic receptors. Examples of classes of agents working apparently by the "monoaminergic hypothesis of depression" include the selective serotonin uptake inhibitors (SSRIs) like fluoxetine, the mixed noradrenaline/serotonin transporter blockers like tricyclic agent imipramine and noradrenaline uptake inhibitors like desipramine. The antidepressant-induced increase in intraneuronal biogenic amines occurs quite rapidly. However, the antidepressant-induced improvement in clinical behavior requires weeks of daily administration.

One hypothesis that may account for the slow-onset of the antidepressants' therapeutic activity is that they work by promoting hippocampal neurogenesis. It is expected that neurogenesis would require a number of weeks for stem cells to divide, differentiate, migrate and establish connections with post-synaptic neurons. The neurogenesis theory of depression then postulates that antidepressant effect is brought about by structural changes in the hippocampal circuitry contributed by newly generated neurons stimulated by antidepressants (Malberg et al., 2000; Czeh et al, 2001; Santarelli et al, 2003).

The neurogenic theory of depression, though not conclusive, has strong supportive data including the finding that neurogenesis is actually requisite for antidepressant behavioral improvement in the novelty suppressed feeding model (Santarelli et al., 2003). A therapeutic benefit from hippocampal neurogenesis is further supported by the finding of hippocampal atrophy in depression, where magnetic resonance imaging studies identified a reduction in the right and the left hippocampal volumes in individuals with major depression (Sheline et al., 1996; Bremner et al., 2000; Mervaala et al., 2000). Long-standing work also suggests a strong relationship between glucocorticoid dysregulation or glucocorticoid hypersecretion in stress and depression, such that the hippocampal volume loss might be considered a consequence of glucocorticoid-induced hippocampal neuronal loss (Sheline et al., 1996; Lucassen et al., 2001; Lee et al., 2002 (review)). Furthermore, in studies which involved the administration of a chronic stress to animals, both hippocampal volume changes and reduction in neurogenesis are observed, and these events are both reversed by chronic antidepressant administration (Czeh et al., 2001; Pham et al., 2003), further illustrating the strong association between depression, stress and neurogenesis. The association comes full circle, since agents or conditions that promote a reduction in neurogenesis also appear as causative agents/events in depression, specifically glucocorticoid (Sapolsky, 2000), and depletion of serotonin (Brezun and Daszuta, 1999). Kempermann and Kronenberg (2003), though acknowledging the validity of the hippocampal neurogenesis theory of depression, suggest that this hypothesis needs to be looked at in the context of a larger model of cellular plasticity, which elucidates how antidepressants include nascent neurons of unknown phenotype to survive and produce viable circuits.

Neurogenesis can be characterized as three successive stages: proliferation of endogenous stem cells and precursors, differentiation into neurons and neuron maturation with formation of viable synaptic connections (plasticity). In consideration of each of these stages of neurogenesis, the hippocampal volume loss in depression could potentially be caused by 1) inhibition of the endogenous hippocampal stem cell proliferation in the dentate gyrus, 2) inhibition of differentiation and dendrite development and 3) loss of neurons (apoptosis) and their dendritic structure. Though apoptosis, also known as programmed cell death, is observed in depression, hippocampal apoptosis, and measured by DNA fragmentation, from depressed patients appears to play only a minor role in the volume loss (Lucassen et al., 2001).

In an animal model of acute stress or in normal animals receiving exogenous corticosterone, the stress causes a reduction in synaptic plasticity in the hippocampus (Xu et al., 1998). Chronic administration of the tricyclic antidepressant, imipramine, partially reversed the loss in long-term potentiation (LTP) in socially stressed, depressive-like animals (Von Frijtag et al., 2001) suggesting imipramine affects the plasticity phase of neurogenesis.

In another animal model of depression characterized by loss of neurogenesis and hippocampal volume loss, stressed animals that chronically receive the antidepressant, tianeptine, show similar numbers of dividing cells as control animals (no social stress) a measure of proliferation (Czeh et al., 2001).

In an experiment looking at association of antidepressants and neurogenesis in normal adult rats, the antidepressant, fluoxetine, required chronic administration to cause proliferation of cells in dentate gyrus (24 hrs post-treatment), but there was considerable loss of nascent cells, whether in the presence or absence of fluoxetine treatment, where fluoxetine provided no observed differentiation or survival benefit (Malberg et al., 2000).

Results on different neurogenic intervention points by known antidepressants suggest that novel neurogenic agents that intervene at different points in the neurogenesis pathway could result in potentially diverse therapeutic effects on depression. These points of intervention can be studied and the target elucidated for novel antidepressant candidates through in vitro assays. Since adult stem cell proliferation and neurogenesis is observed in adult vertebrates in hippocampal dentate gyrus (Gould et al., 2001; Eriksson et al., 1998), we can use multi-potential hippocampal stem cells to screen agents in vitro for neurogenic activity.

Interestingly, chronic administration of either the antidepressant fluoxetine, an SSRI or the antidepressant rolipram, a phosphodiesterase IV inhibitor, promoted neurogenesis in normal animals (Malberg et al., 2000; Nakagawa et al., 2002). One might conclude from these results that any agent that promotes neurogenesis will generate a behavioral benefit in depression, unrelated to the agents' mechanism-of-action or possibly that there is a common pathway where both drug actions overlap. D'Sa and Duman suggest a scheme whereby the phosphorylation and activation of CREB and the subsequent expression of BDNF are central to the induction of neurogenesis that culminates in antidepressant behavior. CREB phosphorylation is increased in animals administered rolipram chronically (Nakagawa et al., 2002), and antidepressants that either increase $Ca^{2+}$/CaM-kinases or cAMP could cause the phosphorylation of CREB in the nucleus (reviewed by D'sa and Duman 2002). D'Sa and Duman (2002) further suggest that the phosphorylated CREB then binds to the CRE binding site to promote the expression of BDNF and bcl-2, that appear critical to cell survival and plasticity. Proof of involvement of neurotrophic factor BDNF in depression comes from studies showing that antidepressants and electroconvulsive shock both caused an increase in BDNF levels (Nibuya et al, 1996) and that intrahippocampal injection of BDNF had antidepressant activity in two models of depression (Shirayama et al., 2002).

If neurogenesis is critical for antidepressant activity is it also sufficient for therapeutic activity and is the mechanism by which the neurogenesis occurs or timing of neurogenesis also critical to the therapeutic activity? These questions can be answered by using novel agents developed through screening paradigms that identify agents that promote the proliferation and differentiation of endogenous hippocampal stem cells to neurons in vivo and determine if they will be effective antidepressants.

In abnormal conditions, such as when an injury to a brain area has occurred, neurogenesis becomes more wide-spread and perhaps functionally diverse. In rodent models of ischemic and hemorrhagic stroke, the newly born neurons of the subependyma (also referred to as subventricular zone) are seen migrating to and accumulating in the lesion area of the cortex. However, the newly born neurons have a short survival period.

Neuropathology associated with key cognitive regions of the Alzheimer's diseased brain has led to therapeutic strategies that address the neuronal loss, in the hopes of reducing the cognitive decline. One strategy enlists trophic agents, that regulate neuronal function and survival, as Alzheimer's Disease (AD) therapeutics (see Peterson and Gage, 1999). Problems with systemic administration, side effects and locating trophic-sensitive neurons generated few clinical successes with these therapies. One AD therapeutic, AIT-082, promotes memory enhancement in AD individual potentially by stimulating endogenous trophic factors (Ritzman and Glasky, 1999; Rathbone et al., 1999). So the use of agents to promote increased survival and function of the remaining available neurons appears to have some therapeutic value.

As discussed, the hippocampus is one of the main brain regions where neurogenesis in adult brain has been documented across several vertebrate species, including monkeys and humans (e.g., Gould et al., 2001; Eriksson et al., 1998). In fact, adult hippocampal neurogenesis contributes functionally to cognitive capacity. Shors et al. (2001) reported that inhibition of neurogenesis in adult rat hippocampus, in the absence of the destruction of existing neurons, caused impaired memory function. Many studies observed that degenerative conditions induced neurogenesis in mature mammalian brains, suggesting the existence of a natural repair pathway by means of neurogenesis. A focal ischemic model, reversible photothrombic ring stroke, caused increased neurogenesis in rat cortex by 3-6% (Gu et al., 2000). Seizures induced by electroconvulsive shock in adult rats increased neurogenesis in dentate gyrus of hippocampus (Scott et al, 2000; Madsen et al, 2000). Also, rats gamma-irradiated to kill mitotic cells in the CNS showed reduced numbers of nascent neurons and reduced LTP in slice cultures. These observations highlight the likelihood that a cellular mechanism for neurogenesis within adult human CNS, especially in hippocampus, does exist both as a normal physiological process and as a self-repairing pathway.

In adult neurogenesis a decline due to aging is observed (Kuhn et al., 1996), though proof that this age-dependent decline in neurogenesis causes cognitive impairment is still debated. Considerable evidence does exit, indicating that increased neurogenesis reduces age-associated cognitive decline. This is most dramatically observed with the transplantation of human stem cells into aged rats initiating improved water maze learning and retention (Qu et al., 2001). Other data suggests that induction of neurogenesis by diet restriction (Lee et al., 2000) exercise (van Praag et al., 1999) or growth factor addition (Lichtenwalner et al., 2001) improves learning and memory in adult or aged rats. A number of other inducers of neurogenesis have been identified, including anti-depressants (Malberg et al., 2000; Czeh et al., 2001), and nitric oxide donors (Zhang et al., 2001) suggesting the usefulness of neurogenic agents for other diseases presenting cognitive-deficits, such as stroke and depression. A small molecule that includes hippocampal neurogenesis that is blood barrier penetrable would allow for a potentially novel oral therapeutic for Alzheimer's disease.

Other potential AD therapeutics progressing in clinical trails, target neurodegeneration in the hopes of reducing the neuronal loss and cognitive decline. Apoptotic death involving caspase pathways and DNA fragmentation has been measured in in vitro and animal models of AD and in Alzheimer's diseased brain tissue. The extend of apoptosis leading to neuronal loss is of continual debate with most agreeing it has some effect, but that other neuronal death pathways definitely play a role (see Behl, 2000; Broe et al., 2001; Roth, 2001). Concern that measures of upstream caspase markers in neurons from AD tissue may not proceed to degeneration has been suggested (Raina et al, 2001). In order to screen for a neuroprotectant therapeutics it is critical, therefore, to measure more than one endpoint of neuronal death and determine at what point an agent may intervene in the death pathway(s). Behl (2000) suggested that AD pathology is most likely a mixture of apoptotic and necrotic pathways and that concentrating therapeutic discovery using only one pathway may provide inconclusive results. All hits in our neurogenesis models were tested through our secondary apoptosis/necrosis assay to screen for agents that function both as neurogenic and neuroprotective agents. These agents may improve or reverse the cognitive decline observed in MCI and AD.

Therefore, recent studies indicate that neurogenesis occurs in the adult human brains under normal as well as under degenerative conditions and that such adult-generated neurons do contribute functionally to the brain physiology such as learning and memory. These observations highlight the likelihood that a cellular mechanism for neurogenesis within adult human CNS, especially in hippocampus, does exist both as a normal physiological pathway and as a self-repairing pathway. What is not known is whether deficiencies in the volume or persistence of neurogenesis and/or the survival or maturation of the new neurons contribute to permanent damage.

Thus, a compound that can stimulate endogenous neurogenesis, either in a disease state or in a healthy state, may be an effective drug for a number of human nervous system conditions and diseases. Many neurological diseases, including Alzheimer's disease, mild cognitive impairment, dementia, age-related cognitive decline, stroke, traumatic brain injury, spinal cord injury, and the like, are neurodegenerative conditions. Neuropsychiatric diseases including depression, anxiety, schizophrenia and the like also show nerve cell dysfunction leading to cognitive, behavioral, and mood disorders. A neurogenic drug or agent that enhances the process of generating new neurons (neurogenesis) would be beneficial for countering and treating these diseases.

Candidate drugs generated from the screening have been tested in various animal models of human neurological and psychiatric disorders to determine the drugs' therapeutic potentials. An effective, predictive in vitro assay that can be used to select for clinical drug development neurogenic compounds that is particularly effective in promoting the neurogenesis in vivo has been described in U.S. patent application Ser. No. 10/728,652 filed Dec. 5, 2003, which is incorporated herein by reference in its entirety.

SUMMARY

The present invention relates to compounds that promote neurogenesis in vivo. More particularly, the present invention is related to classes of compound structures that are shown to be particularly effective in promoting neurogenesis including compounds of the type, fused imidazoles, aminopyrimidines, nicotinamides, aminomethyl phenoxypiperidines and aryloxypiperidines. These compounds are shown to promote neurogenesis by proliferation and/or differentiation of human hippocampal multipotent stem cells and/or progenitor cells and neuronal progenitors. Moreover, the present invention relates to these agents as therapeutics for prevention and treatment of neurological diseases in mammals and as reagents for detecting neurogenesis and proliferation.

In one embodiment of the present invention, compounds are evaluated for their ability to promote neurogenesis by proliferation/differentiation of human hippocampal multipotential stem cells and neuronal progenitors and whether small molecule agents of the above chemical structures that have neurogenic activity in vitro and/or in vivo also have the ability to inhibit neuronal death. Modulation of neurogenesis pathways may overlap pathways critical to apoptotic and necrotic neurodegeneration, therefore, neurogenic small molecule agents are tested for their ability to inhibit neurodegeneration.

The compounds of the present invention are shown to stimulate endogenous neural stem cells capable of differentiating into neurons in adult human brains to proliferate and to differentiate into functional neurons in vivo. The additional neurons may enhance the cognitive ability of the subject and significantly extend the ability to perform cognitive tasks during extended periods of sleep deprivation.

The present invention also includes the identification of a specific class of compounds, the aminopyrimidines, that appear especially effective at inhibiting apoptosis in various neurodegenerative models suggesting this class of compounds might be especially useful for neurodegenerative indications.

The present invention includes neurogenic drugs which serve to prevent or treat neurodegenerative and neuropsychiatric disorders by promoting the endogenous birth of new neurons within the nervous system by administering the compounds of the present invention to the patient alone or in combination with transplanted stem cells or progenitor cells.

In a further embodiment of the present invention, the compounds are used as reagents for detecting neurogenesis and proliferation in an in vitro assay.

In one embodiment of the present invention, an agent is administered to treat a neurodegenerative disease. In a preferred embodiment of this invention the neurodegenerative disease includes Alzheimer's disease, dementia, mild cognitive impairment, aged-related cognitive decline, Parkinson's disease, amyotrophic lateral sclerosis, multiple sclerosis, demyelination, stroke, spinal injuries, traumatic brain injuries, neuropathic pain, and the like.

One embodiment of the present invention includes an agent administered to treat a psychiatric disease. In one embodiment, the psychiatric disease includes depression, post-traumatic stress syndrome, acute or chronic stress, anxiety, schizophrenia, sleep deprivation, cognitive dysfunction, amnesia, and the like.

One embodiment of the present invention includes an agent administered by any number of routes including combining with multipotent stem cells or differentiated multipotent stem cells transplanted into brain.

In yet another embodiment of the present invention, the agent is administered to treat a cognitive dysfunction, memory deficit, or decreased learning capacity.

In a further embodiment of the present invention, cognitive dysfunction includes sleep deprivation, moderate cognitive impairment (MCI), and the like.

In another embodiment of the present invention, the agent is administered to enhance cognitive function, memory, and/or learning capacity of an individual.

In another embodiment of the present invention, an agent is administered by at least one route and at least one multipotent stem cell or differentiated multipotent stem cell is transplanted into brain.

In another aspect of the present invention, the agent is utilized in the above methods. Additional features and advantages of the present invention are described in, and will be apparent from, the following Detailed Description of the Invention and the figures.

Additional features and advantages are described herein, and will be apparent from the following Detailed Description and the figures.

BRIEF DESCRIPTION OF THE FIGURES

(FIG. 9B) or vehicle alone (FIG. 9A) for ten days. The animals were injected daily with BrdU for the first seven days. At the end of the ten-day periods, the animals were perfused and their brains sliced for immunostaining with anti-BrdU antibody, and analysis. FIG. 9B illustrates that the NSI-158 treated brain has far greater dividing cells in the dentate gyrus of the hippocampus than vehicle treated mouse as illustrated in FIG. 9A.

DETAILED DESCRIPTION

Figure 1:
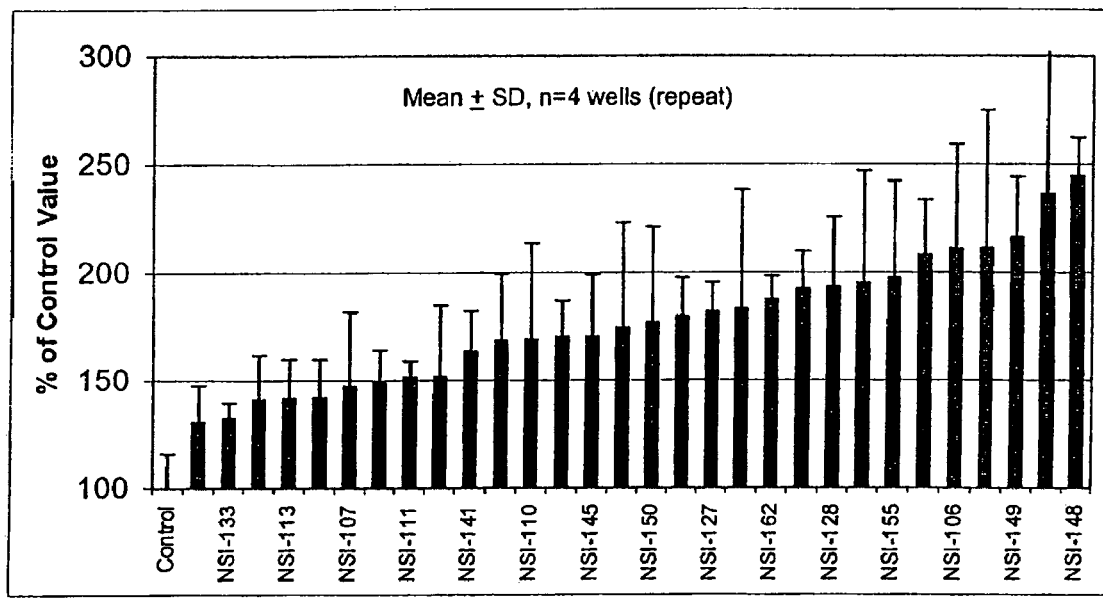
FIG. 1 is a bar graph illustrating an example of a proliferation profile of compounds selected from primary screening. Proliferation is measured after compound treatment for seven days by Alamar Blue staining of live cells per well. Shown are relative values over the vehicle control.

The present invention relates to the identification of a specific type of compounds including fused imidazoles, aminopyrimidines, nicotinamides, aminomethyl phenoxypiperidines and aryloxypiperidines for use as therapeutic agents and analytical reagents by means of promoting neurogenesis by proliferation/differentiation of human hippocampal multipotent stem/progenitor cells and neuronal progenitors. More particularly this invention relates to these agents as therapeutics for prevention and treatment of neurological diseases in mammals and reagents for detecting neurogenesis and proliferation.

The key activity of a neurogenic agent is to increase the number of neurons generated from their precursors. A neurogenic agent can bring about such an increase in the number of neurons by a number of different mechanisms. The neurogenic agent can increase the number of neurons generated from their precursors (neurogenesis) and/or can protect existing neurons from neurodegeneration (neuroprotection).

The neurogenic agent can increase neurogenesis by acting as a mitogen for the neutral stem/progenitor cells and, thereby, increasing the progenitor's cell number which, in turn, results in increased number of neurons in the culture when differentiated. Another mechanism includes the neurogenic agent acting as a neuronal specification factor by promoting the stem/progenitor cell differentiation toward neurons at the expense of glia. This directed differentiation will also result in increased number of neurons in the culture, but without changing the overall cell number. In yet another mechanism, the neurogenic agent can act as a mitogen for committed neuronal progenitors that differentiate only into neurons. Increasing this subpopulation would also increase the final number of neurons in the culture. Alternatively the neurogenic agent can act as a neuroprotectant to decrease neurodegeneration by acting as a survival factor to rescue immature neurons from undergoing cell death during differentiation, which will result in increased neurons.

Initial compound libraries include directed-libraries based on mechanistic pathways or targets thought to be involved in mitosis, differentiation, and survival of neural cells. These targets include growth factor receptors (e.g., FGFR, EGFR, NGFR), signal transduction pathways such as ras, CREBP, protein kinases and phosphatases, cell-cycle regulators such as c-myc, p53, p21, transcription factors such as bHLH proteins and nuclear hormone receptors, extracellular membrane (ECM) proteins such as metalloproteinases, and stress-related factors. These targets represent a collection of non-overlapping pharmacophores which cover diverse chemical space and, at the same time, lead to rapid identification of structure-activity relationships.

A neurogenesis screen of components to discover a safe drug which can activate the stem cells within the brain of a subject, especially in the hippocampus, and which can recruit new neurons into the circuitry to broaden the neural functionality at the physiological level must be capable of identifying a compound that will significantly boost either of these processes. In vitro assay in 96-well format have been designed to detect the effect of a compound on the proliferation and differentiation of hippocampal stem cells. These assays have been used to screen compound libraries for activities that stimulate mitosis and/or differentiation of hippocampal stem cells and/or progenitors. Candidate drugs generated from the screening will be tested in various animal models of human neurological and psychiatric disorders to determine the drugs' therapeutic potentials.

The compounds identified as potential neurogenic agents include compounds with the following general structures:

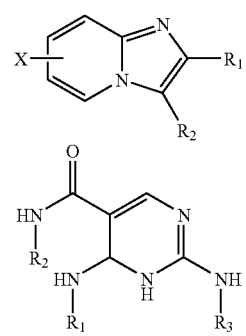

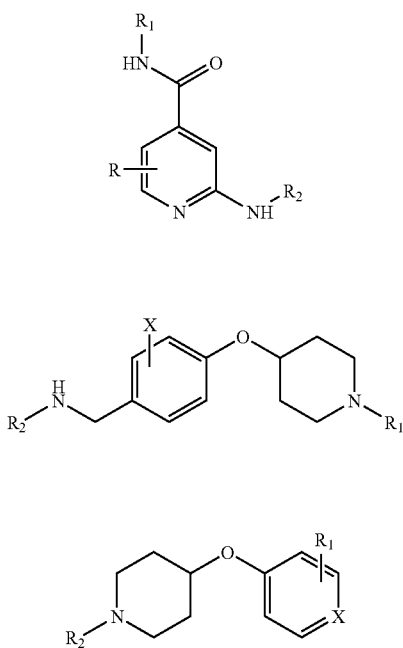

Culturing a Stable Cell Line of Neural Progenitors

A screening of a large number of unknown agents (e.g., protein factors, peptides, nucleic acids, natural compounds, or synthetic compounds) for discovering a candidate drug involves repeating the same test for hundreds to millions of times. This repeated testing requires high level of reproducibility from the test. In order to obtain such reproducibility for a neurogenesis assay, stable cell lines of neural progenitors are required which, upon differentiation, generate reproducible quantities of neurons. For this purpose, a cell line is defined as a population of cells having been expanded for at least ten cell-doublings.

Human and other mammalian neural stem cells have been isolated, expanded, and differentiated, in culture from all major areas of the brain and spinal cord. (See for example, U.S. Pat. No. 5,753,506 and U.S. Pat. No. 6,040,180). Hundreds of stable, characterized, and cryopreserved neural stem cell lines have been isolated from many areas of the human and rodent brains including the hippocampus. In one embodiment, a multipotent neural stem cell/progenitor cell line derived from human hippocampus is used. As discussed above, the hippocampus is known for its relatively high level of neurogenesis. Cell lines derived from other areas of the central nervous system (CNS), including the dentate gyrus of an adult brain, can also substitute for the hippocampus. A neural progenitor population derived as a stable cell line from partial differentiation of embryonic stem cells can also be used.

Although cell lines that are not genetically engineered are preferred, in one embodiment, cell lines that are genetically engineered to enhance the mitotic capacity of the cells are used to test potential neurogenic agents. In one embodiment, the genetic modification consists of intracellular over-expression of functional c-myc protein under a conditional activation system such as a c-myc protein fused to a ligand-binding domain of an estrogen receptor as described in U.S. patent application Ser. No. 09/398,897 and filed Sep. 20, 1999, and incorporated herein by reference.

In one embodiment, a progenitor population that, upon differentiation, generates both neurons and glia in a single culture has been used. Presence of glia, either astrocytes and/or oligodendrocytes, or their precursors, are required to promote physiological maturation of nascent neurons born from their precursors in culture.

In one embodiment, differentiation of the progenitors is initiated by withdrawing the mitogen from the culture. It is preferable that serum as well as other growth-promoting factors, are removed from, or not added to, the differentiating culture due to their significant effect on the reproducibility of the neurogenesis assay.

Detection of Cell Proliferation

Neural stem cells and progenitor cells differentiate spontaneously in the absence of a mitogen; therefore, undifferentiated mitotic cells are harvested by enzyme treatment to remove residual mitogen, such as basic fibroblast growth factor (bFGF) used in expansion and proliferation of the cells. In one embodiment of the present invention, undifferentiated human hippocampal stem cells (e.g., HH580)/progenitor cells are harvested by enzyme treatment.

The collected cells are seeded for attachment of the cells such as standard 96-well or 384-well plates, pre-coated with extracellular matrix proteins, such as poly-D-lysine and fibronectin (e.g., Biocoat PDL, Fisher). The initial seeding density can be within the range of about 2,000-125,000 cell per well of a 96-well plate. The preferred density, however, is 40,000 cells per well of a 96-well plate which has been optimized for best signal-to-noise ratio as described in pending U.S. patent application Ser. No. 10/728,652. Cell density that is too low retards the initiation of differentiation and results in poor plating efficiency which interferes with the assay. Cell density that is too high leads to inhibition of neurogenesis due to cell-to-cell interaction and paracrine factors which also interfere with the assay. It should be appreciated that the actual cell number can be proportionally decreased or increased depending upon the surface area of the culture substrate used. For example, for a 384-well plate which has approximately one-fourth of the surface area of a 96-well plate, the initial seeding density should be decreased by one-fourth accordingly.

The cells are passaged and grown for seven days in 15 cm plates in full growth medium according to Neuralstem protocol with 50% of the medial changed every other day. Following centrifugation, the cell pellet is re-suspended in $N_2b$ medium and enough $N_2b$ medium is added to the cell suspension to achieve a concentration of $4 \times 10^5$ cells per ml. The $N_2b$ seeding media includes a standard serum-free, growth factor-free, basal media without phenol red that supports healthy neuronal/glial survival. Fibronectin and PBS is completely removed by aspiration from wells of fibronectin-coated 96-well plate(s). 100 μl of $N_2b$ medium with or without 2x concentration of screening agents or compounds to be tested are added to each well. Subsequently, 100 μl of the cell suspension is added to each well at a density of 40,000 cells per well. The cell suspension is incubated for two days at 37° C. in the presence of 5% $CO_2$.

On Days 2, 4, and 6 of post-plating, incremental additions of the compounds are made to each well at appropriate concentrations. Therefore, after two days, 100 μl of $N_2b$ medium is removed from the wells, and 100 μl of the $N_2b$ medium is added. Likewise, on days four and six, 100 μl of $N_2b$ medium is removed from the wells and 100 μl of the $N_2b$ medium is added, and the cell suspension is again incubated at 37° C. in the presence of 5% $CO_2$.

One day seven, the final day of the culture, a fluorescent dye such as Alamar Blue dye is added to each well. Alamar Blue dye detects metabolic respiration and is a reflection of total cellular activity indicating changes in cell number of neurons. In this regard, 20 µl of Alamar Blue (Biosource International DAL 1025) is added to each well and incubated for two hours at 37° C. in the presence of 5% $CO_2$.

As a preliminary detection of positive activities, the overall immunostaining intensity in each well is read by a fluorescence plate reader. For instance, the fluorescence of the oxidized dye in each well is read by a fluorescent plate reader such as the Molecular Devices Fluorometric Plate Reader. The reader is set on the Read Mode End Point setting at an excitation of 530 nm, an emission of 590 nm, and a cutoff 570 nm. The fluorescence level is proportional to the number of respiring cells in the culture and is a measure of a proliferation activity of a test agent. The data is then exported and saved into any suitable database such as a Microsoft Excel Workbook.

FIG. 1 illustrates the level of proliferation of the cells after treatment with a number of compounds described in Tables I and II for seven days by Alamar Blue staining of live cells per well. The measurement of proliferation is represented by a relative ratio of neurons expressed as a percentage of the total cells for each compound to the total cells for the vehicle control. The typical ratio of neurons to the vehicle control is 40-50%. The ratio can change by either increased differentiation of stem cells to neurons, decreased proliferation of astrocytes, or increased proliferation of neuronal progenitors.

After the Alamar Blue assay to detect general cellular proliferation, further staining with other markers are required to determine what cell types (e.g. neuronal, glial) are observed under differentiating media.

Detection of Neurogenesis

The final neuron number is detected by immunostaining of the culture with antibodies against neurons and is quantified by counting of the immunopositive neurons and/or by measuring the staining intensity. Therefore, after seven days of compound treatment, the cells are stained with the neuron-specific anti-tubulin IIIb antibody, TuJ1, for neurons and Hoechst for all cell nuclei. The number of TuJ1+ neurons per area is quantified and expressed as a value relative to the vehicle-treated control of Hoechst-stained cells. In this regard, the medium is removed from the wells by decanting and blotting the plates on paper towels. The cells are then fixed in 100 µl of 4% paraformaldehyde per well for thirty minutes at room temperature. The cells are washed three times with 400 µl per well of phosphate-buffered saline (PBS) at pH 7.5 for approximately ten minutes per wash. The plates are then stored at 4° C. in PBS or used immediately for staining.

The cells are subsequently stained with antibodies against neuron-specific antigens according to standard procedures. The staining process includes decanting the PBS and blocking the cells with 100 µl of 5% Normal Goat Serum (NGS) in PBS for one hour at room temperature. The NGS/PBS is decanted and the plates are blotted on a paper towel. The cells are then permeabilized with 0.1% Triton X-100 in PBS for 30 minutes at room temperature.

Typical neuron-specific antigens include Type III-beta tubulin and MAP-2c. The total cell number in each well was quantified by staining the cultures with a nuclear dye such as DAPI or Hoechst according to standard procedures. Therefore, once the cells are permeabilized, 20 µl of TuJ1, monoclonal antibody against neuronal class III β-tubulin (CoVance (BabCo) MMS-435P) and 32 µl of anti-GFAP polyclonal (DAKO Z0334) are added to and mixed of PBS with 5% NGS. Final dilutions of TuJ1 and anti-GFAP are 1:400 and 1:250, respectively. 90 µl of the antibody solution is added to each well except two eleventh column. 90 µl of PBS/5% NGS is added to the eleventh column and no cells are added to the twelfth column. The plate(s) are sealed with parafilm and incubated at 4° C. overnight.

After incubating the cells overnight, the antibody solution is decanted and 200 µl of PBS/0.1 % Triton X-100 is added to the wells. The plate(s) s are placed on a shaker and incubated at room temperature with gentle shaking for ten minutes. The cells are again washed with the PBS/Triton X-100 solution another two times.

Following staining with TuJ1 and anti-GFAP, 20 µl of Alexa Fluor 488 labeled goat anti-mouse IgG (H+L) (Molecular Probes A-I1001) and 100 µl of LRSC-IgG, goat anti-rabbit (Jackson Immuno 111-295-144) is added and mixed with 10 ml of PBS/5% NGS. 100 µl of the resulting antibody solution is added to each well. The plate(s) are covered with foil and incubated with gentle shaking for up to one hour at room temperature. The cells are again washed as described above with PBS and an Triton X-100. 200 µl of PBS is then added to each well and microscopy is performed to detect positive TuJ1 and GFAP staining.

If the cells are not positive for TuJ1 and GFAP staining, one 20 µl aliquot of DAPI (Molecular Probes) or Hoechst (Sigma Chemical) is diluted in 2 ml of PBS. 20 µl of this solution is then added to each well. The plates are left at room temperature for 15 minutes and then washed twice with PBS. After a final wash 200 µl of PBS is added to each well.

The plate(s) are then read by the Molecular Devices Fluorometric Plate Reader to determine the ratio of TuJ1+ cell number (neurons) to Hoechst-strained cells (total cells). The reader is set on the Read Mode Well Scan setting. For detection of TuJ1/Alexafluor 488 staining the settings include an excitation wavelength of 495 nm, emission wavelength of 519 nm with auto cutoff, and a PMT Sensitivity set on high. For detection of GFAP/LRSC staining, settings include an excitation wavelength of 570 nm, an emission wavelength of 590 nm with auto cutoff, and a PMT Sensitivity set on medium. For detection of DAPI/Hoechst staining the excitation is set at 358 nm, the emission is set at 461 nm with auto cutoff, and the PMT Sensitivity is set on high.

Figure 2:
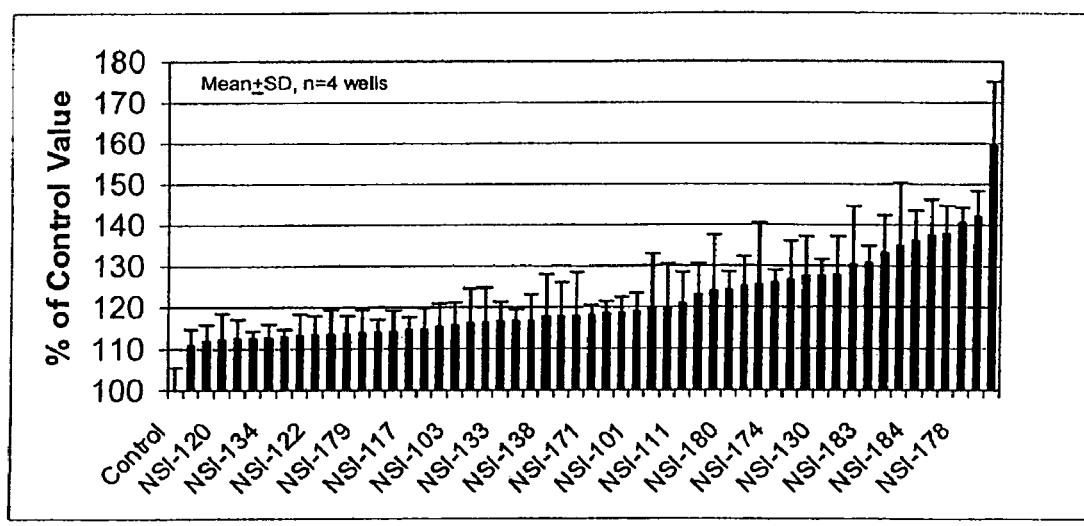
FIG. 2 is a bar graph illustrating an example of a neurogenesis profile of compounds selected from primary screening. After seven days of compound treatment, the cells were stained with the neuron-specific anti-tubulin IIIb antibody, TuJ1, for neurons and Hoechst for all cell nuclei. Shown are the relative ratio of neuron: total cells for each compound over the vehicle control in percentage. Typical ratio for vehicle control is 40-50% neurons. The ratio can change by either increased differentiation of stem cells to neurons, decreased proliferation of astrocytes, or increased proliferation of neuronal progenitors.
Figure 3:
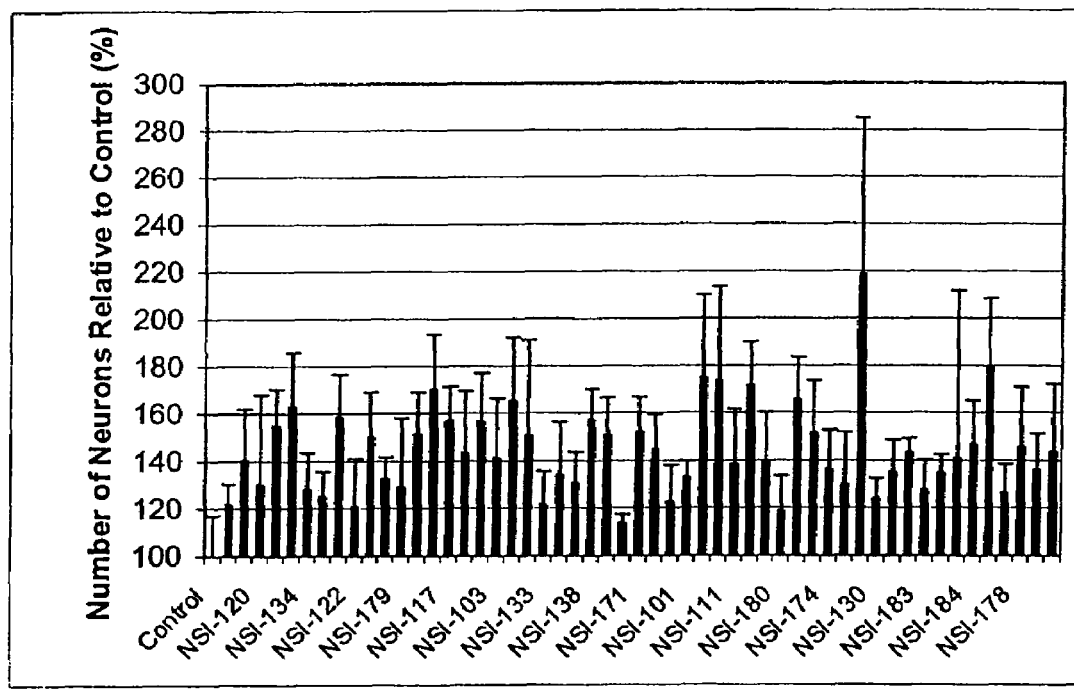
FIG. 3 is a bar graph illustrating an example of a neurogenesis profile of compounds selected from primary screening. After seven days of compound treatment, the cells were stained with TuJ1 for neurons. The number of TuJ1+ neurons per area was quantified and expressed as a relative value to the vehicle treated control.

FIG. 2 for example illustrates an example of a neurogenesis profile of compounds selected from primary screening which provides the relative ratio of neurons expressed as the total cells for each compound as a percentage of the total cells for the vehicle control. The typical ratio of neurons to the vehicle control is 40-50%. To this end, a compound with 130% or greater Alamar Blue reading compared to that of the vehicle control is selected as an active compound for the proliferation effect. A compound with 110% or greater increase in the neuronal number or the neuronal proportion over the control as indicated by immunostaining using other markers is selected as an active agent for the neurogenic effect. For the positive hits, more quantitative analysis is carried out by automated morphometric counting of individual cells.

Primary Screening of Unknown Compounds

Synthetic organic compounds for screening through the neurogenesis screen are pre-selected by predicted bioavailability and CNS permeability. Calculations for CNS permeability is based on the use of 300 descriptors for 1,474 known CNS therapeutics. Predicted properties for successful CNS drugs are determined to be: (1) molecular eight (MW) of 400 or less, (2) five or fewer hydrogen bond acceptors, (3) two or fewer hydrogen bond donors, (4) polar area below 120 angstrom, and (5) neutral or basic with a pKa between 7.5 and 10.5.

Since the screening of 10,000 small molecule compounds in in vitro models of neurogenesis has been completed the in vitro screen have been shown to be predictive of in vitro neurogenic efficacy, orally available agents can be tested, that promote in vivo neurogenesis in models of depression.

Rolipram, for example, an antidepressant that works by increasing cAMP levels and is neurogenic in animals (Nakagawa et al., 2002) was effective in a primary in vitro neurogenesis screen. This suggests that the primary in vitro screen includes those agents that might promote neurogenesis by targeting the cAMP/pCREB/BDNF pathway. This does not necessarily exclude all other neurogenesis mechanisms for the neurogenesis agents. If the target of these neurogenic agents is important for behavioral activity where three separate chemically diverse classes showed in vitro assay efficacy differences and that the mechanism for all does not overlap at the point of CREB phosphorylation and BDNF expression then one might expect very different effects on behavioral activities in depression models.

Cumulatively, over five thousand synthetic compounds of the type including fused imidazoles, aminopyrimidines, nicotinamides, aminomethyl phenoxypiperidines and aryloxypiperidines have been evaluated for their effect on neurogenesis according to the assay methods described above. From the preliminary analysis using the fluorescent plate reader, over three hundred compounds show initial positive activity. Those three hundred compounds have been re-analyzed by quantitative neuron counting. Among them, thirty compounds significantly increase cell number or proliferation; fifty-three compounds increase the number of neurons neurogenesis; and seven demonstrated significant activity in both proliferation and neurogenesis. The significance level was empirically set at an activity above 30% change over the vehicle control for proliferation and above 10% change for neurogenesis.

Sixteen compounds possessing exceptional in vitro neurogenic capacity have been identified and are listed along with their structures in Table I. The sixteen compounds have been tested for neurogenic activities in live mice as described below and in in vitro assays. Table II details the efficacy results of the sixteen effective small molecule agents. Based on these findings, the compounds have potentially effective therapeutic value for any number of neurodegenerative and neuropsychiatric disorders. These disorders include, but are not limited to, stroke, Alzheimer's disease, Parkinson's disease, depression, mild cognitive impairment (MCI), traumatic brain injury and the like.

Dose-Response Profiles

In another in vitro assay, compounds are tested as above at varying concentrations to obtain a dose-response curve and EC50 values (effective concentration of the compound which produces 50% of the maximum possible response for that compound). Compounds with EC50 values below 10 µM for neurogenesis or proliferation effect are considered further.

Figure 4:
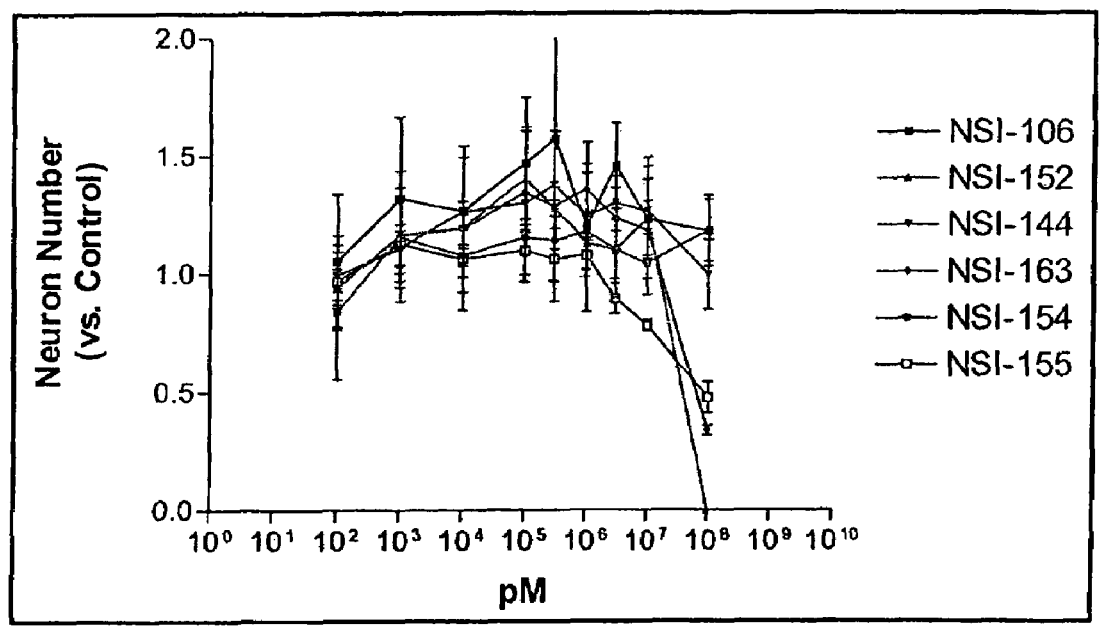
FIG. 4 is a line graph illustrating an example of aneurogenesis dose-response profile of selected compounds. Differentiating human hippocampal stem cells were treated for seven days with varying concentrations of "primary hits". Subsequently, the cells were fixed, stained with anti-beta tubulin antibody, and positive cells were quantified by ArrayScan II. Shown are the number of neurons after each treatment normalized against the no-compound control.

Primary dose-response profiles and secondary functional assays are used to further eliminate compounds from the primary screen based on a lack of dose-dependent effect on neurogenesis, indicated by lack of linearity of dose-response, and in vitro neurotoxicity. The dose-response curve measures neurogenesis over a concentration range of 100 pM to 100 µM. Examples of several primary hits fully analyzed for dose-response are shown in FIG. 4. Significantly, most compounds exhibit a linear response over several log concentrations below 1 µM. This linear response indicates that the assay for primary screening is reliable and that the quality of the compound library is high. Table II contains the summary of EC50 of each compound tested. On the other hand, at high concentrations such as 100 µM, some, but not all, compounds tested showed a high level of neurotoxicity, indicating that analyzing dose-response curves will be discriminatory and serve as an effective early filter.

Detection of Neuroprotection

Agents that promote proliferation and neurogenesis are further evaluated for their ability to inhibit neurodegeneration and apoptosis of the human hippocampal multipotent stem cell-derived neurons. Neurodegeneration may be induced in culture using any number of inducers as known by those skilled in the art. Examples of neurodegenerative inducers include: staurosporine, hypoxia reperfusion, free radicals, glutamate agonists, activated monocyte supernatant, beta amyloid peptides and corticosteroids to name a few. Some of the neurogenic agents inhibit loss of neurons, inhibit caspase activation, inhibit nuclear fragmentation or condensation, inhibit lactate dehydrogenase activity among other effects on neurodegeneration. Using staurosporine as an example, 125 nM of a staurosporine solution is added along with 10 µM of one of the listed neurogenic agents to human hippocampal stem cells differentiated for 3-4 weeks.

A number of neurogenic agents inhibit neuronal loss, caspase-3 activity and/or nuclear fragmentation compared to staurosporine vehicle control. These NS1 small molecule agents are all effective at in vitro neurogenesis as determined by methods described. More particularly, human hippocampal stem cells differentiated for a period of 3-4 weeks are treated with an agent for 8-24 hrs in a neuronal maintenance media prior to treatment with an apoptotic or neurodegenerative insults such as staurosporine, TNFα and LPS-stimulated monocyte supernatant and the like. Following the treatment period, media is removed from the treated cells and the cells are fixed and stained. Staining may include Hoechst stain, MAP-2ab (AP-20) antibody staining, active caspase-3 antibody or other measures of neurodegeneration and apoptosis. Instrumentation such as a Molecular Devices fluorescent plate reader or a Cellomics Array Scan II instrument and the like may be used to measure the degeneration and apoptosis.

Figure 5:
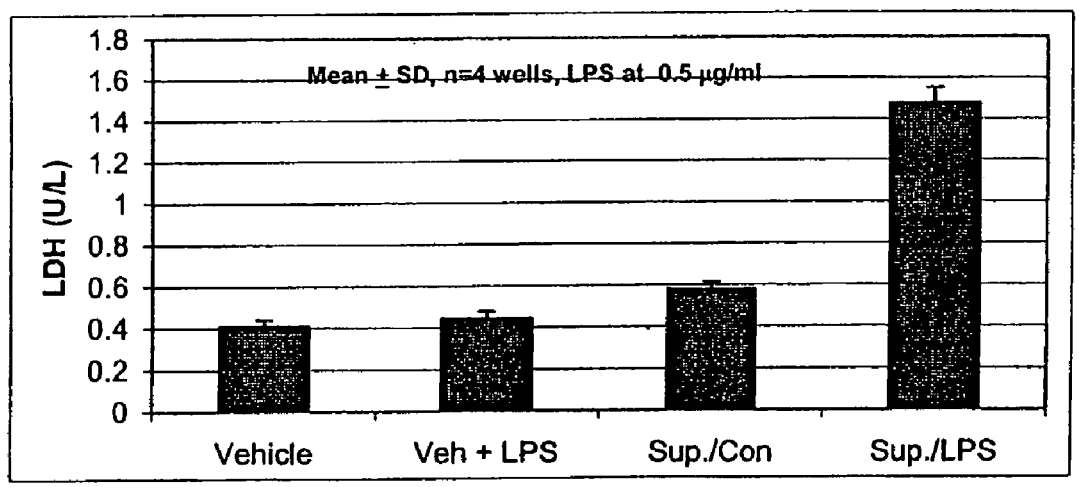
FIG. 5 is a bar graph illustrating an example of results of an assay for an in vitro model of neuroinflammation. Human hippocampal stem cells were differentiated for four weeks and then treated with the spent medium collected from human monocytes pre-treated for twenty-four hours with either the vehicle alone (RPMI medium)or with 0.5 ug/ml lipopolysaccharide (LPS). Lactate dehydrogenese (LDH), a number of neuroinflammation, in the neuronal culture media are measured twenty-four hours post incubation of the hippocampal cells with the monocyte supernatants.

FIG. 5 illustrates the results of an assay for an in vitro model of neuroinflammation. One secondary screen for neuroprotection being used in one embodiment of the present invention includes an in vitro model that physiologically mimics stress. Since a large body of literature suggests that stress-induced consequences on cells are mediated by cytokines and other pro-inflammatory agents, cellular stress induced by neuroinflammation in culture is available as a reasonable approximation of the neuroinflammation process in human brains. Thus, a secondary assay to measure the effect of a compound to protect neurons from LPS-activated human monocyte supernatant is established.

Figure 6:
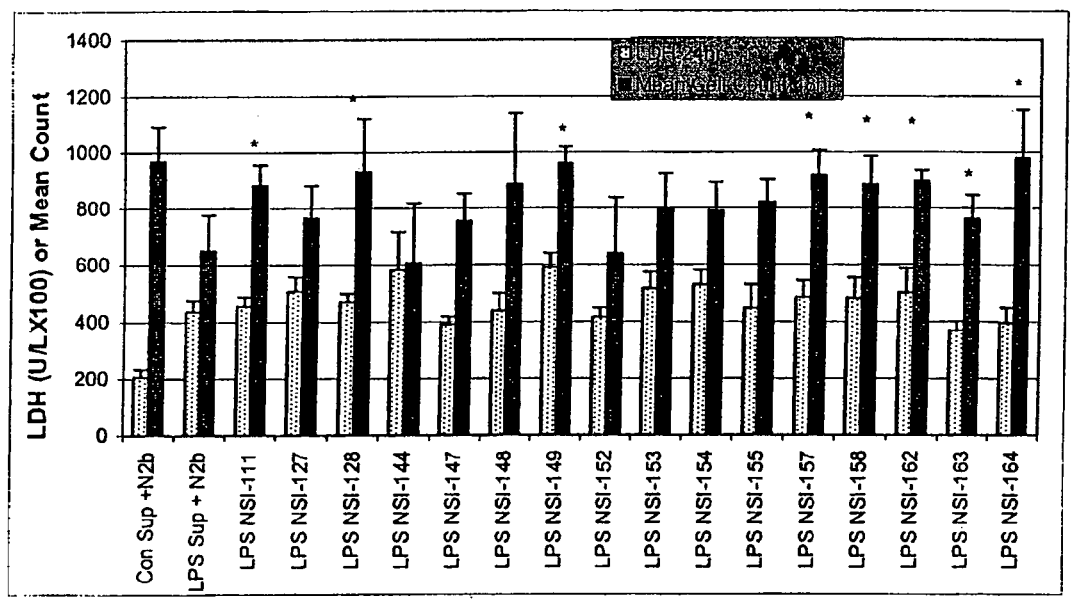
FIG. 6 is a bar graph illustrating an example of a neuroprotection profile of the compounds in the neuroinflammation assay. Human hippocampal stem cells were differentiated for four weeks and then treated with the spent medium collected from human monocytes pre-treated for 24 hours with either the vehicle alone or with 0.5 ug/ml lipopolysaccharide (LPS). LDH in the neuronal media was measured at 24 hours post incubation of the hippocampal cells with monocyte supernatant while the number of neurons indicated by MAP-2 staining was measured after forty-eight hours of treatment.

As illustrated in FIGS. 5 and 6, the results of the assay include LDH release, which measures cell damage/death, and the actual cell counting of neurons. Human hippocampal stem cells are differentiated for four weeks and then treated with the spent medium collected from human monocytes pretreated for twenty-four hours with either the vehicle alone (RPMI medium) or with 0.5 ug/ml lipopolysaccharide (LPS). Lactate dehydrogenese (LDH) in the neuronal media was measured at 24 hours post incubation of the hippocampal cells with monocyte supernatant while the number of neurons indicated by MAP-2 staining, was measured after forty-eight hours of treatment. As illustrated in FIGS. 5 and 6, the results of the assay include LDH release, which measures cell damage/death, and the actual cell counting of neurons.

In FIG. 6, of the sixteen compounds tested by this secondary assay, one compound demonstrated protection measured by LDH release at 24 hours post-treatment and seven showed neuroprotection measured by counting of neurons at 48 hours post-treatment.

Method for Measuring Caspase-3 Activity as a Measure of Apoptosis

Another assay used to determine the ability of a compound to provide neuroprotection is an apoptosis assay. Apoptosis is measured using the activity of an early marker of the programmed cell death pathway, caspase-3. Following 24 hours or 48 hours of apoptotic-induction in the presence and absence of compound treatment, the media is removed from the wells, and 50 µl cell lysis buffer is added to each well. 50 µl of 2X reaction buffer containing 10 mM DTT is then added to the lysate in each well. The contents of two wells are combined (for example: rows A/H, B/G, C/F, D/E), and 5 µl of substrate is added per well as recommended in the protocol for a caspase-3 fluorometric assay kit (Biovision) known in the art. The plate is incubated at 37° C. for 60 minutes. The contents of each well are then transferred to a fresh plate, and the fluorescence is determined with an emission wavelength of 400 nm and an excitation of 505 nm using a fluorescent plate reader such as the Molecular Devices Gemini Fluorescent Plate Reader. Caspase-3 activity is expressed as µM of cleaved substrate per hour. Substrate concentration in µM is run for each plate to determine activity values for each treatment condition.

Figure 7A:
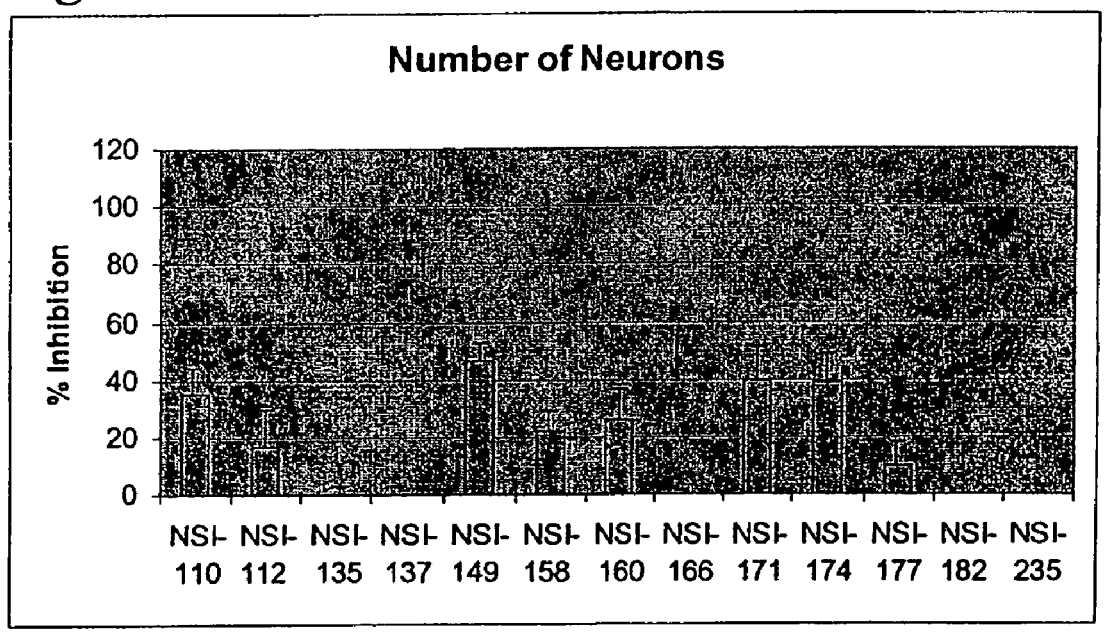
FIG. 7A is a bar graph illustrating an example of a neuroprotection profile of the compounds against staurosporine-induced human hippocampal neurodegeneration as indicted by loss of neurons after twenty-four hour treatment with staurosporine by counting the remaining number of neurons, an increased in nuclear fragmentation, and an increase in intracellular levels of activated caspase-3/-7 detected by immunostaining. Addition of 125 nM staurosporine solution to human hippocampal stem cells differentiated for 3-4 weeks causes neuronal injury and death. Effect of the compound treatment to inhibit the staurosporine-induced neuronal loss and injury are shown. Each bar represents n=6 wells of the mean +/− the SEM from a single experiment.
Figure 7B:
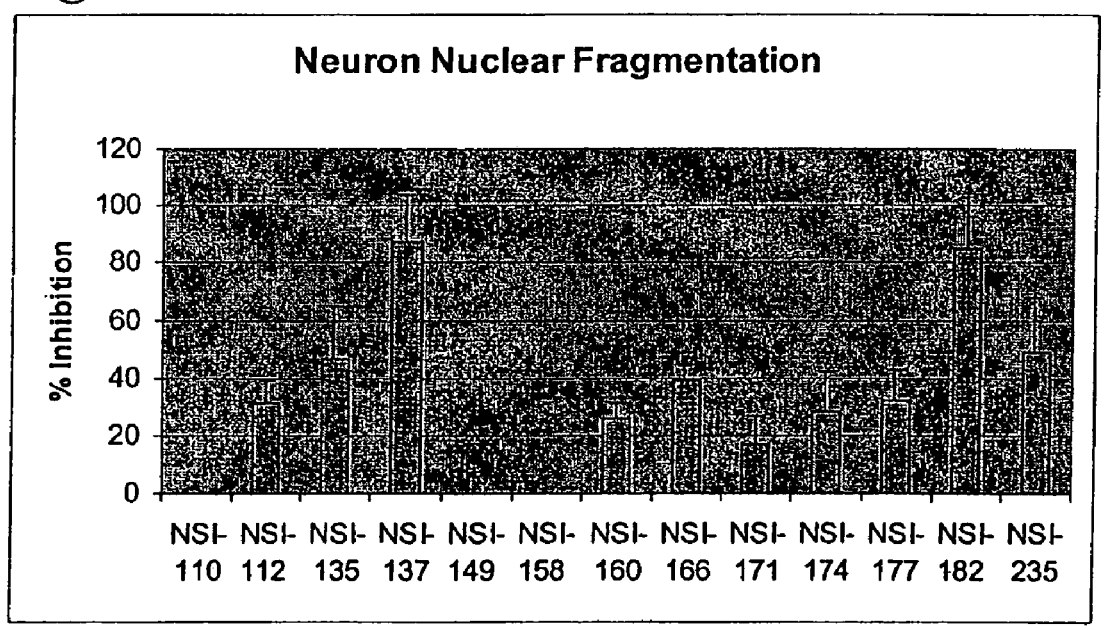
FIG. 7B is a bar graph illustrating an example of a neuroprotection profile of the compounds against staurosporine-induced human hippocampal neurodegeneration as indicted by an increase in nuclear fragmentation after twenty-four hour treatment with 125 nM staurosporine solution to human hippocampal stem cells differentiated for 3-4 weeks. Effect of the compound treatment to inhibit the staurosporine-induced neuronal loss and injury are shown. Each bar represents n=6 wells of the mean +/− the SEM from a single experiment.
Figure 7C:
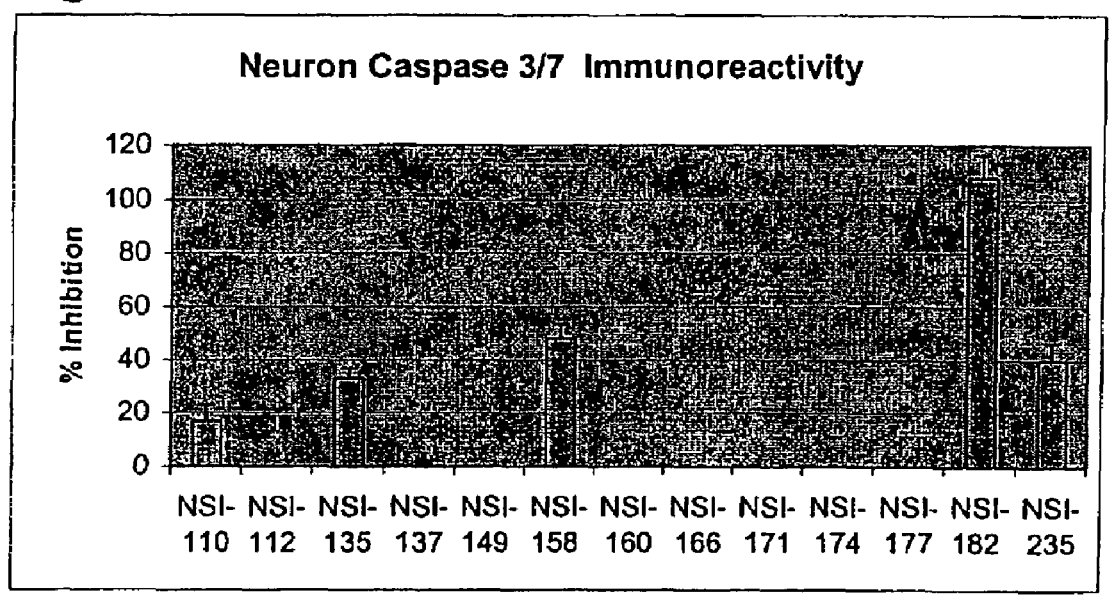
FIG. 7C is a bar graph illustrating an example of a neuroprotection profile of the compounds against staurosporine-induced human hippocampal neurodegeneration as indicated by an increase in intracellular levels of activated caspase-3/-7 detected by immunostaining after twenty-four hour treatment with 125 nM staurosporine solution to human hippocampal stem cells differentiated for 3-4 weeks. Effect of the compound treatment to inhibit the staurosporine-induced neuronal loss and injury are shown. Each bar represents n=6 wells of the mean +/− the SEM from a single experiment.

FIGS. 7A, 7B and 7C illustrate an example of a neuroprotection profile of tested compounds against staurosporine-induced human hippocampal neurodegeneration measured by the remaining number of neurons, an increase in nuclear fragmentation, and an increase in intracellular levels of activated caspase-3/-7 detected by immunostaining, respectively. Human hippocampal stem cells that have been differentiated for 3-4 weeks undergo a twenty-four hour treatment with 125 nM staurosporine solution to cause neuronal injury and death. The effect of the compound treatment to inhibit the staurosporine-induced neuronal loss and injury is shown in each of FIGS. 7A, 7B and 7C. Each bar represents n=6 wells of the mean +/− the SEM from a single experiment.

Figure 8:
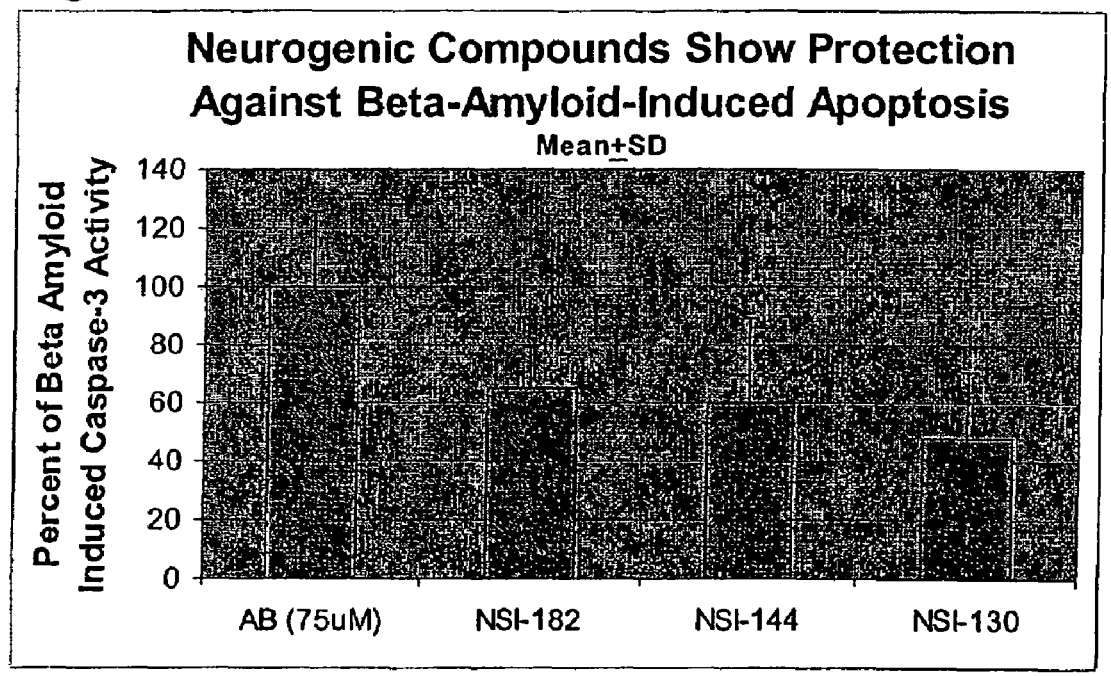
FIG. 8 is a bar graph illustrating an example of a neuroprotection profile of the compounds against apoptosis, also known as programmed cell death, induced by beta amyloid peptide 25-35 as a model of Alzheimer's disease. Caspase-3 activation plays a central role in apoptosis and is an indicator of the occurrence of apoptosis if detected. Shown are three agents, NSI-182, NSI-144 and NSI-130, that inhibit apoptosis induced by beta amyloid peptide 25-35. Bars represent mean±SD from five wells.

FIG. 8 is a bar graph illustrating an example of a neuroprotection profile of the compounds against apoptosis induced by beta amyloid peptide 25-35, part of a larger peptide found in plaques in Alzheimer's brains, as a model of Alzheimer's disease. Caspase-3 activation plays a central role in apoptosis and is an indicator of the occurrence of apoptosis if detected. Three of the compounds, NSI-182, NSI-144 and NSI-130, are shown to inhibit apoptosis induced by beta amyloid peptide 25-35. Bars represent mean±SD from five wells.

In Vivo Neurogenic Effects of NSI Compounds

Figure 9:
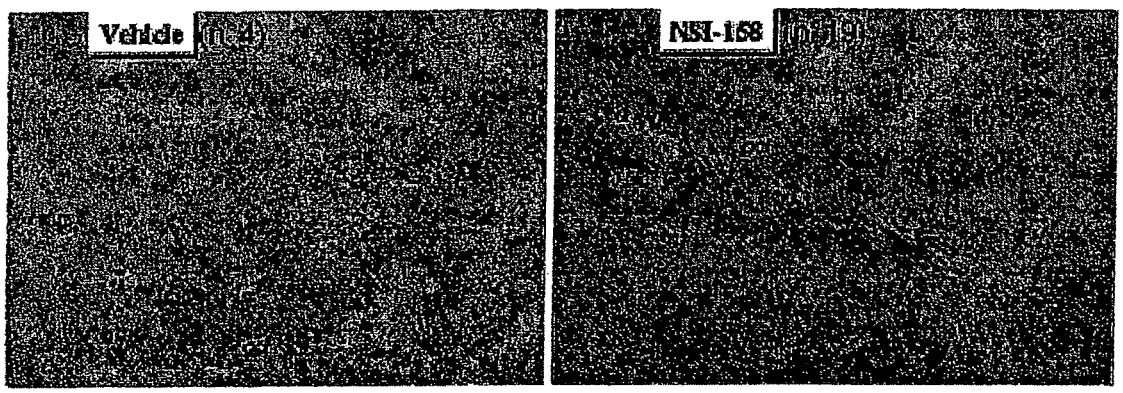
FIG. 9A and FIG. 9B are micrographs illustrating an example of BrdU immunostaining of a mouse dentate gyrus having been administered a vehicle and a compound. Mice were treated daily with various test compounds at 10 mg/kg p.o.

In one embodiment, fifteen of the compounds from Table I above are administered orally to mice at 10 mg/kg for ten days and co-administered bromodeoxyuridine (BrdU) by intraperitoneal injection for the first six days. One class of compounds caused a significant increase in neurogenesis. This class, broadly defined as "isonicotinamides" and, more specifically of the structures, NSI-189 and NSI-158, were especially effective at promoting neurogenesis in the dentate gyrus of C57B16 adult mice following ten-day consecutive oral administration. For example, in FIGS. 9A and 9B, BrdU immunostainings of hippocampal slices from two mice treated with either vehicle alone or NSI-158 are illustrated. In FIGS. 9A and 9B, the mice are treated daily for ten days with vehicle alone (FIG. 9A) or orally with various test compounds at 10 mg/kg (FIG. 9B). The animals are injected daily with BrdU for the first seven days. At the end of the ten-day period, the animals are perfused and their brains sliced for immunostaining with anti-BrdU antibody and analysis. FIG. 9B illustrates that the NSI-158-treated brain has far greater dividing cells in the dentate gyrus of the hippocampus than the vehicle treated mouse illustrated in FIG. 9A. Therefore, it is apparent that, compared to the vehicle treatment, the NSI-158 treatment caused an increase in dividing cells in the dentate gyrus, especially in the granular cell layer which is made up of only neuronal cells.

Figure 10A:
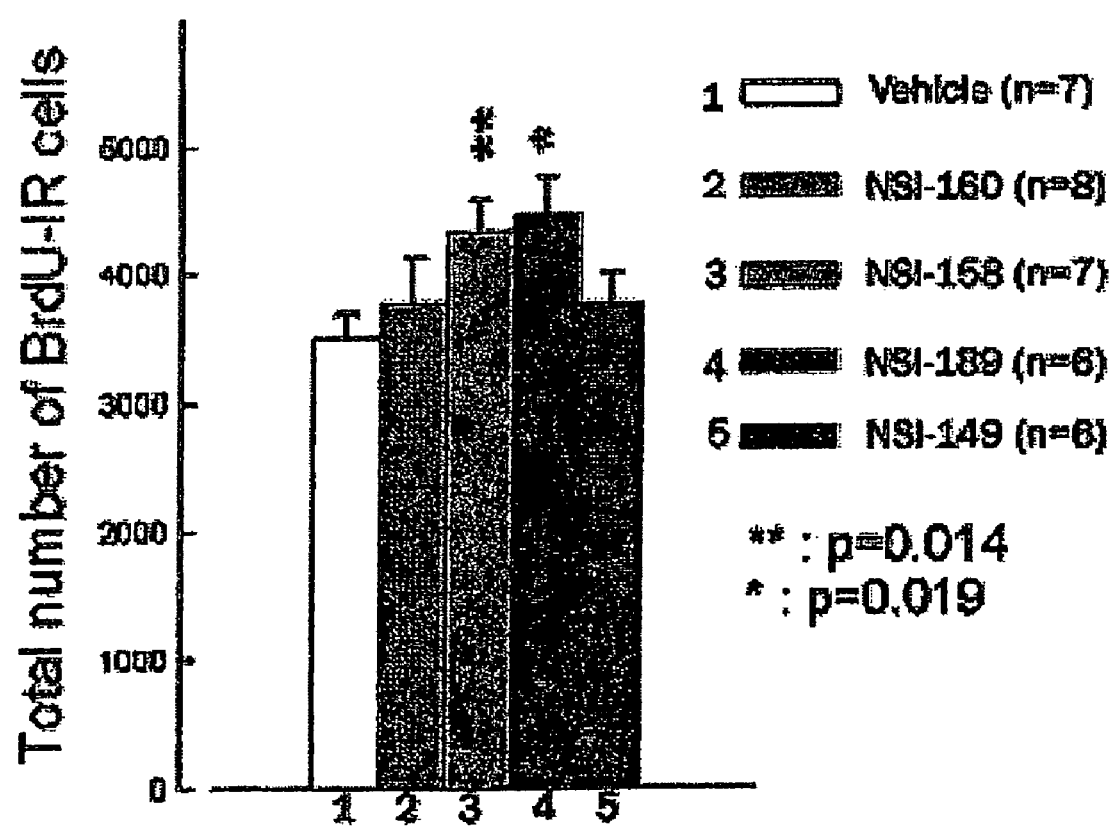
FIGS. 10A and 10B are bar graphs illustrating an example of quantification of BrdU-immunopositive cells in the in vivo neurogenesis testing the compounds. Mice were treated with the various test compounds for in vivo neurogenesis in two cohorts. The post-mortem cell counts of BrdU-immunopositive cells of the two cohorts are shown in FIGS. 10A and 10B. The cells from one dentate gyrus of each mouse in each test group were counted and average BrdU values immunoreactivity are shown. The symbols, * and ** indicate immunoreactivity increases of statistical significant the indicated p values. Seven compounds are especially effective in increasing the neurogenesis in the dentate gyrus of the healthy adult mice, the area known to have continued adult neurogenesis.
Figure 10B:
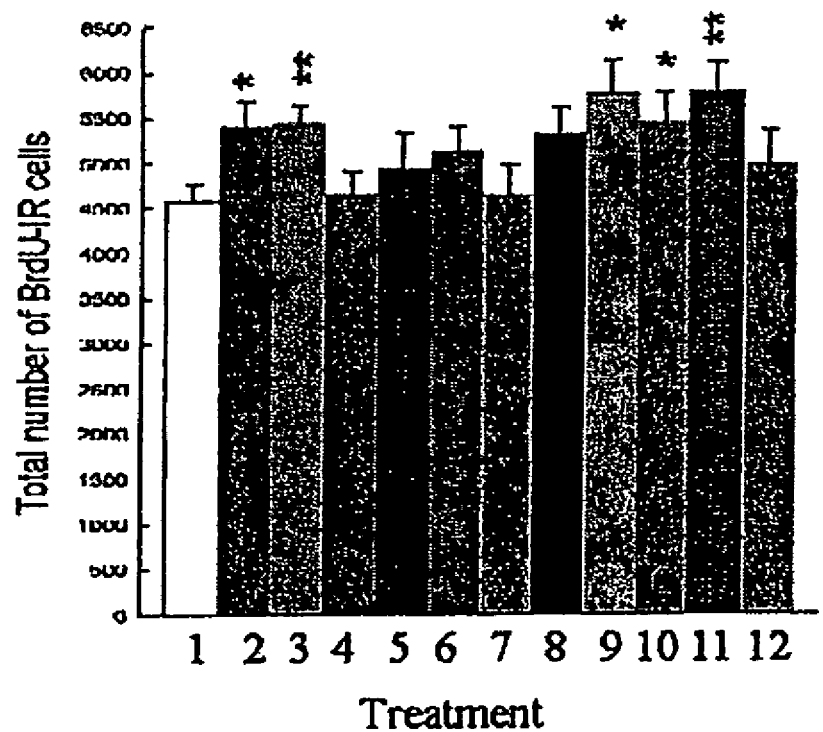

In FIGS. 10A and 10B, seven compounds are demonstrated to be especially effective in increasing neurogenesis in the dentate gyrus of healthy adult mice. Mice were treated with the various test compounds for in vivo neurogenesis in two cohorts as described above. The cells from one dentate gyrus of each mouse in each test group were counted and average BrdU immunoreactivity values are calculated. The post-mortem cell counts of BrdU-immunopositive cells of the two cohorts representing an absolute number of dividing cells indicate increased neurogenesis as shown in FIGS. 10A and 10B. The symbols, * and ** indicate immunoreactivity increased of statistically significant p values.

The ability to promote in vivo neurogenesis using these orally administered compounds suggest that these agents could be beneficial for a number of disease states including depression, aging, stroke, Alzheimer's disease and mild cognitive impairment, to name a few. With the production of new neurons in the granular cell layer these same compounds could promote cognitive enhancement to counteract loss of neurons due to disease, injury or age. These could be useful when cognition enhancement in humans might be beneficial for military and other purposes. It should be appreciated that other potential uses are contemplated herein and that this list includes only some of the potential uses for which these neurogenic agents appear ideally suited.

Further Studies of NSI-Compound Effects on the Stages of In Vitro Neurogenesis

In another in vitro assay, compounds of the fused imidazole, aminopyrimidine, nicotinamide, aminomethyl phenoxypiperidine and aryloxypiperidine types are evaluated for their effect on the differentiation of the culture-born cells to mature neurons. More particularly, multipotent human hippocampal stem cells are treated in three doses over a one-week period in N2b media and in the presence of an agent of the type mentioned above. The cells are then fed twice weekly for approximately two more weeks in N2b or Neuralbasal+ B27 Media (Gibco) and then cells are fixed using 4% paraformaldehyde. Cells are washed 3X with PBS (pH 7.4) and then stained using a nuclear stain (Hoechst or DAPI) and a mature neuronal marker, MAP-2ab (AP-20) antibody. A secondary antibody, Alexa Fluor 488 labeled goat anti-mouse IgG, is used to identify by fluorescent labeling the mature neurons. The fluorescent intensity and number of cells labeled in a multi-plate format can be measured using for instance a Array Scan II (Cellomics) or similar instrumentation.

Figure 11:
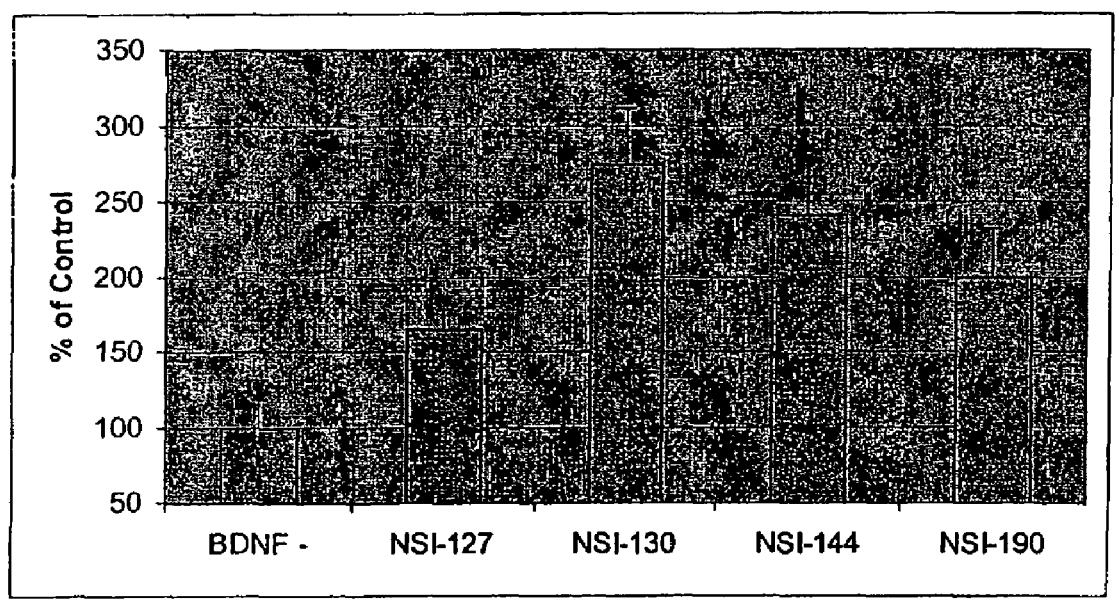
FIG. 11 is a bar graph illustrating an example of in vitro neurogenesis profile of the compounds for a long-term treatment. Differentiating hippocampal human stem cells were treated with vehicle alone or with the test compounds for three weeks. Increase in cell number was determined compared to the control. Shown are several examples that are effective in continued neurogenesis. Bars represent mean +/− SD from six wells.

Effects of the long-term NSI compound treatment on human hippocampal stem cells in the absence of mitogen is illustrated in FIG. 11. FIG. 11, differentiating hippocampal human stem cells are treated with vehicle alone or with the test compounds for three weeks. Increase in cell number was determined compared to the control. Bars represent mean +/− SD from six weeks. FIG. 11 demonstrates that an increase in neuronal number with two weeks of treatment (5X with 10

μM) occurs beyond that observed previously with just one week of treatment with anNSI compound. Several examples of NSI compounds are shown to be effective in continued neurogenesis. For example, NSI-130 and NSI-144 in addition to being particularly effective in inhibiting apoptosis due to beta amyloid as discussed above, are also effective in stimulating further increases in neuron numbers over a relatively long time period which may be advantageous for agents that are useful in chronic diseases such as Alzheimer's disease. These agents comprise a class of compounds, aminopyrimidines, that, as shown previously, inhibited apoptosis. Accordingly, the aminopyrimidine class of compounds appear ideally suited for neurodegenerative long-term diseases including Alzheimer's disease and aging. Neurogenic agents that are neuroprotective like the sixteen compounds identified above might also be effective therapeutics for other neurodegenerative diseases in mammals including, but not limited to, stroke, traumatic brain injury, Parkinson's disease, and mild cognitive impairment.

Figure 12:
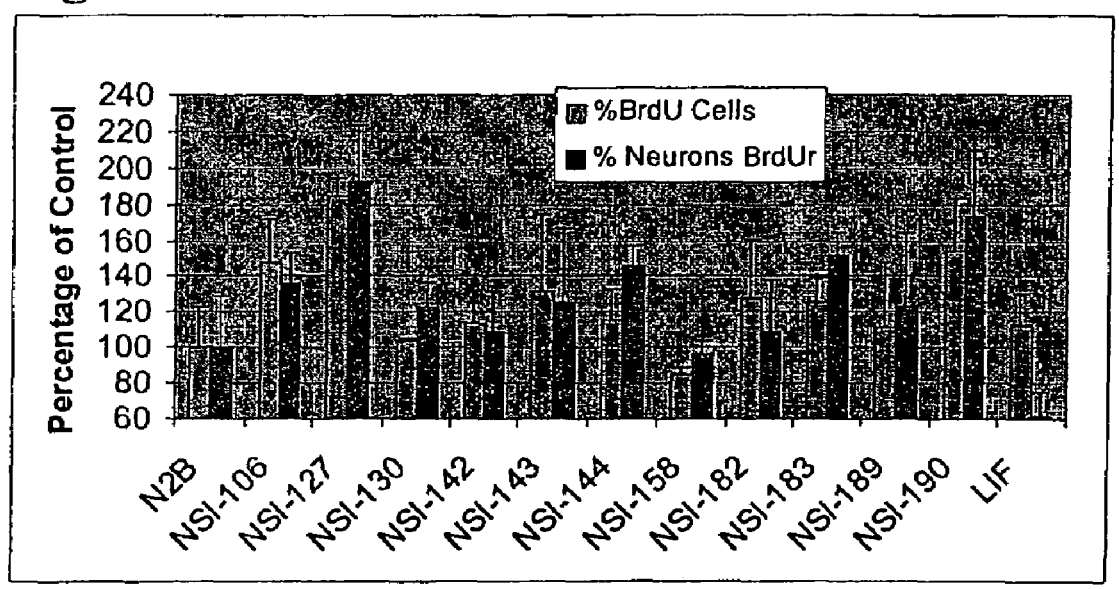
FIG. 12 is a bar graph illustrating an example of differentiation into mature neurons as a percentage of control in response to a three-week treatment with the test compounds. Mitotic cells were labeled with BrdU. BrdU-positive cells ere double-stained with the marker of mature neurons, anti-MAP-2 antibody. Total BrdU-immunostained cells and BrdU+/MAP-2ab+ co-stained cells indicating neurons were counted.

In FIG. 12 the exact number of dividing cells and neurons are determined to confirm that the increase in neurons is due to proliferation followed by differentiation. In FIG. 12, hippocampal stem cells are plated in a 96-well plate. The cells are then treated with one of the agents listed along with a two-day pulse of bromodeoxyuridine which is taken up into dividing cells thereby labeling mitotic cells with BrdU. After three weeks of continuous treatment with the listed agents, the cells are fixed and stained for BrdU immunoreactivity. BrdU-positive cells are double-stained with the marker of mature neurons, anti-MAP-2 to identify cells that have differentiated into mature neurons. The BrdU+/MAP-2ab+co-stained cells which have differentiated into mature neurons are distinguished from control BrdU-immunostained cells which are proliferating stem cells. A number of agents, especially NSI-127, NSI-144, NSI-183 and NSI-190 appear to induce proliferation and then differentiation into neurons into the second and third week following the removal of stem cell mitogen.

Figure 13:
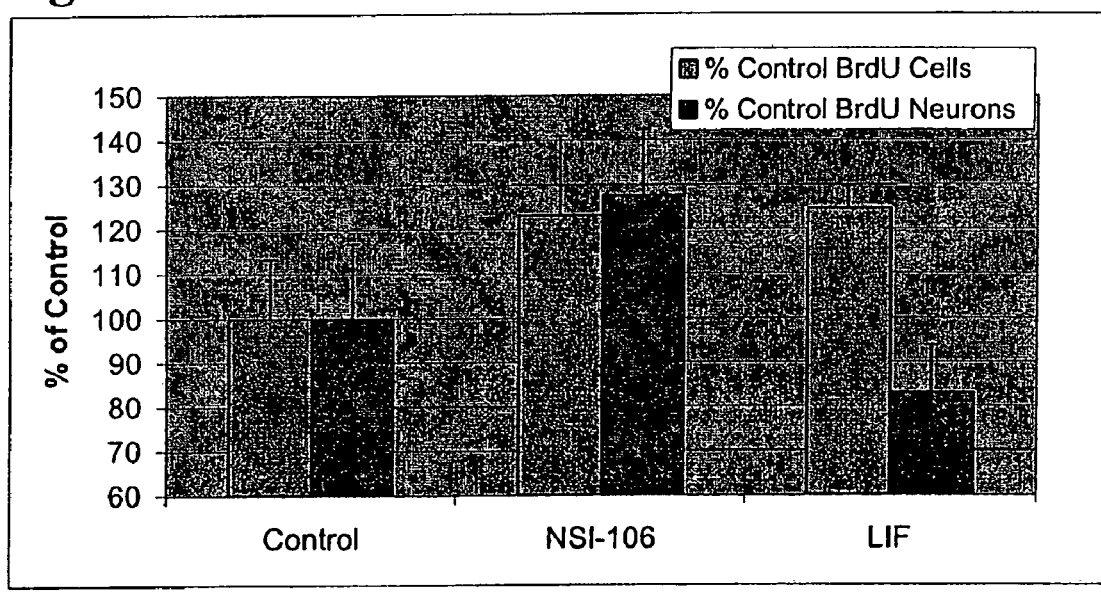
FIG. 13 is a bar graph illustrating an example of neuronal identification of the mitotic cells in response to the compound treatment. Mitotic cells were labeled with BrdU during the last forty-eight hours of the two-week treatment with the test compounds. BrdU alone and BrdU together with TuJ1 as co-stained cells were quantified. Results from NSI-106 and LIF treatment are shown as an example. Unlike with LIF, NSI-106 produces mostly co-stained cells, indicating that the mitotic population is committed neuronal progenitors. The bars represent the mean±SD from each of six wells.

As illustrated in FIG. 13, one NSI compound provided as a continuous treatment for ten days further increases the number of dividing cells compared to the seven-day treatment suggesting that the proliferation phase of neurogenesis continues past the first week. The results of the assay further suggest that the proliferation involves a committed neuronal progenitor. In FIG. 13, mitotic cells are labeled with BrdU during the last forty-eight hours of a two-week treatment with the test compounds. BrdU alone and BrdU together with TuJ1 as co-stained cells are quantified.

As described in pending U.S. patent application Ser. No. 10/728,652, leukemia inhibitory factor (LIF), a cytokine growth factor, was selected from among several known neurotrophic factors as a positive control against which tested compounds can be compared. The selection of LIF as a positive control was based on its properties to increase the number of neurons and glia by two to three-fold. This effect is both consistent with the neural stem cell system in which the cells respond appropriately to the positive control by enhanced differentiation and/or mitosis, and achieves the objective of the assay method in which such cellular responses can be measured reproducibly and quantifiably. Thus, the use of LIF in FIG. 13 is as a positive control to discriminately test agents for selectively possessing neurogenic activity.

Results from NSI-106 and the positive control, LIF treatment are shown as an example. Unlike with LIF, NSI-106 produces mostly co-stained cells, indicating that the mitotic population is committed neuronal progenitors. The bars represent the mean±SD from each of six wells.

Figure 14:
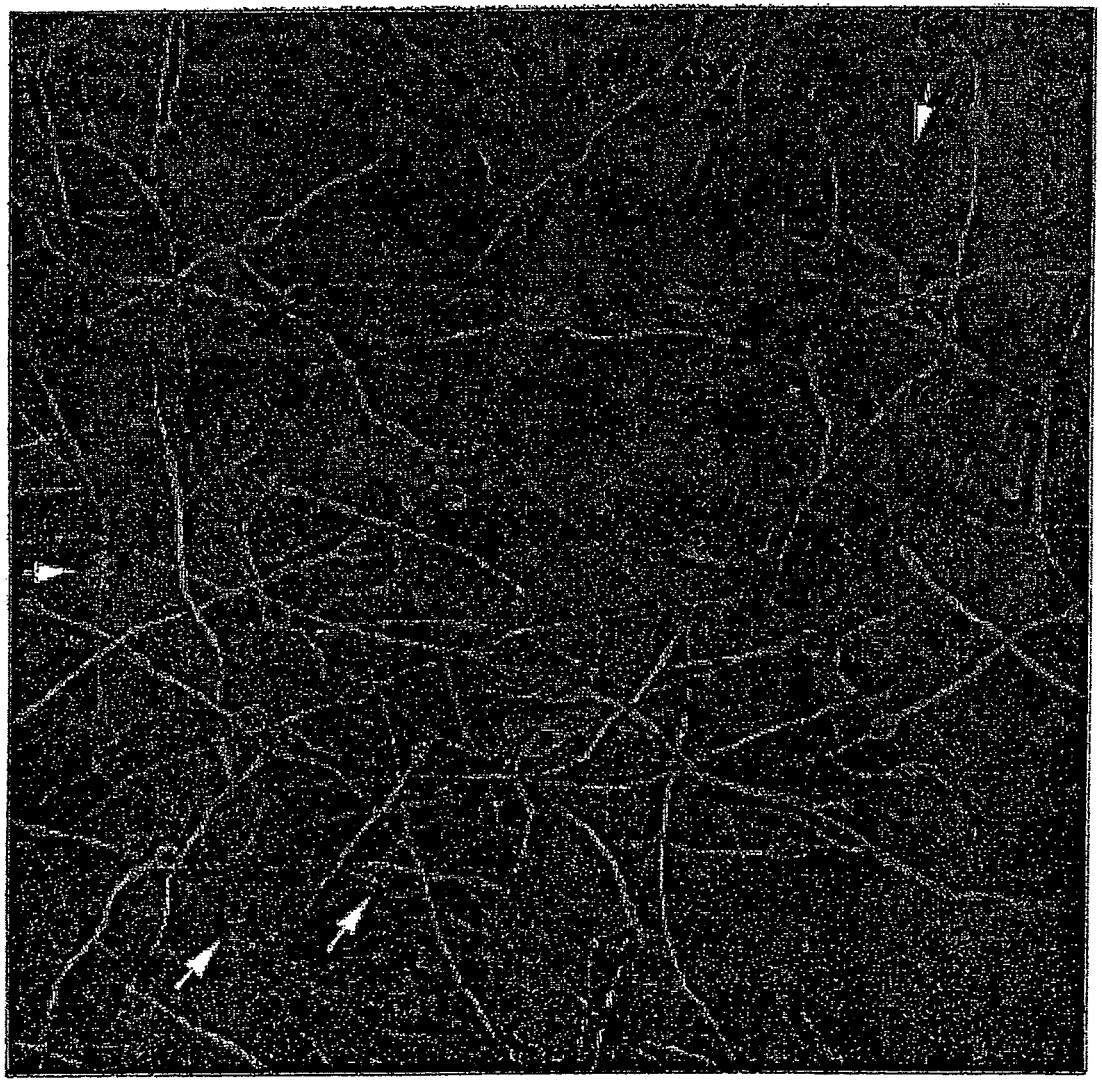
FIG. 14 is a micrograph illustrating an example of production of committed neuronal progenitors by NSI-106. Differentiating hippocampal stem cells were treated with NSI-106 for 10 days, fixed, and stained for Ki-67 protein as well as TuJ1. Ki-67 protein is an endogenous marker of motosis. Significant number of cells were co-stained suggesting that NSI-106 not only increases the number of dividing stem cells but causes increase in dividing neuronal precursors or committed neuronal progenitors as indicted by Ki-67 positive and TuJ1 positive cells demonstrating neuronal morphology.

FIG. 14 illustrates committed neuronal progenitor production by NSI-106. Differentiating hippocampal stem cells are treated with NSI-106 for 10 days, fixed, and stained for Ki-67 protein to detect dividing cells as well as TuJ1 to detect cells that have differentiated into neurons. Ki-67 protein is an endogenous marker of mitosis. As illustrated in FIG. 14, significant number of cells are co-stained as indicated by Ki-67 positive (blue nuclei) and TuJ1 positive (strongly green) cells demonstrating neuronal morphology. This observation suggests that NSI-106 not only increases the number of dividing stem cells but causes an increase in dividing neuronal precursors or committed neuronal progenitors.

In addition, referring back to FIG. 8, possible neuronal progenitors include cells with neuronal morphology seen with Ki-67 positive and TuJ1 positive in response to NSI-106 treatment after one week of human hippocampal stem cells in the absence of mitogen.

The compound NSI-106 and similar agents could be useful especially in a more lipophilic form, as understood by those skilled in the art to promote division of neuronal progenitors in brain. This agent could be useful for a number of neurological indications. This agent and those like it, even in its present form, could be useful with any endogenous or transplanted stem cell to promote a neurogenic phenotype. The neurogenic phenotype could then be used for purposes of reversing or improving any number of neurological indications. For example, this agent could be given in utero or early postnatally for the purpose of improving brain or spinal nerve development. This compound might also be useful in stimulating embryonic stem cells to produce a neuronal progenitor that could be differentiated into neurons. Other uses of such a compound include hippocampal replenishment of neurons replacing, replenishing or enhancing any neuronal phenotype in brain, spinal cord and peripheral nervous system. This compound could then be useful for not only CNS indications but any nerve cell disease or injury.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

TABLE I

| NSI # | CLogP | Structure |
|---|---|---|
| 106 | 3.166 | 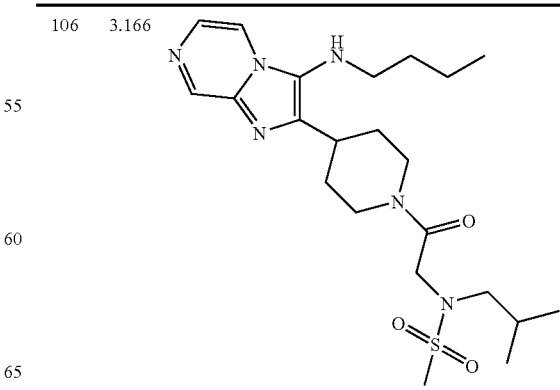 |

TABLE I-continued
| NSI # | CLogP | Structure |
|---|---|---|
| 127 | | 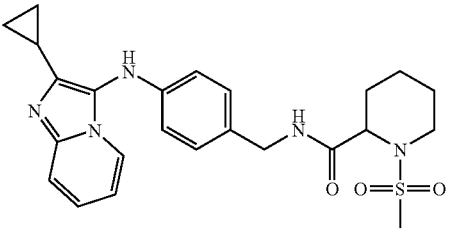 |
| 130 | 3.12 | 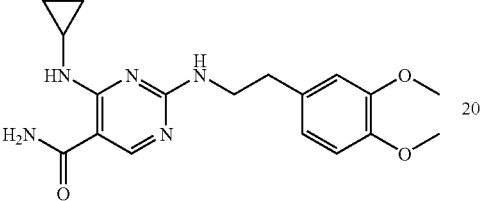 |
| 142 | | 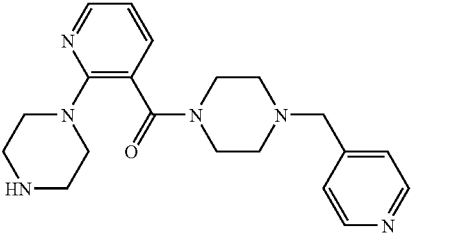 |
| 143 | 1.44 | 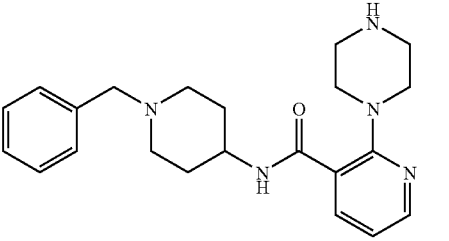 |
| 144 | | 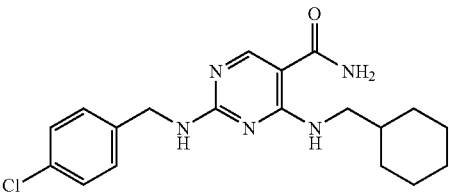 |
| 149 | | 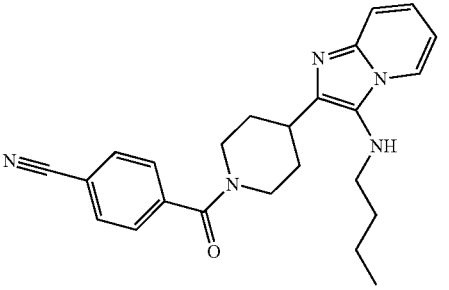 |
| 150 | | 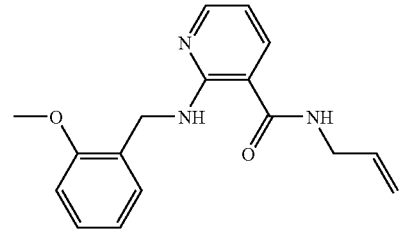 |
| 157 | | 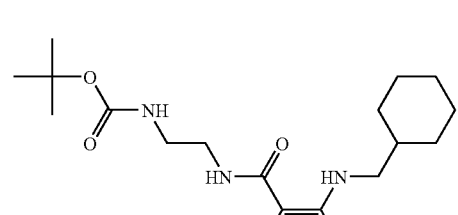 |
| 158 | |  |
| 182 | 3.01 | 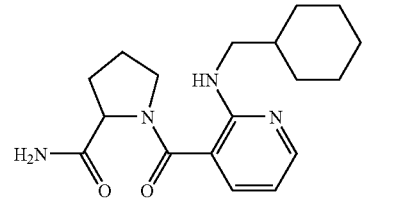 |
| 183 | | 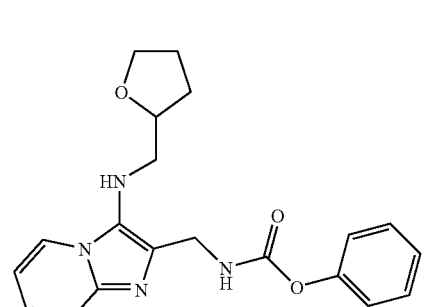 |

TABLE I-continued

| NSI # | CLogP | Structure |
|---|---|---|
| 185 | | 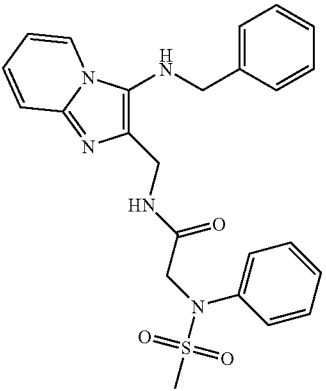 |
| 189 | 4.497 | 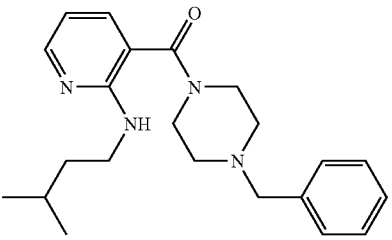 |
| 190 | 4.32 | 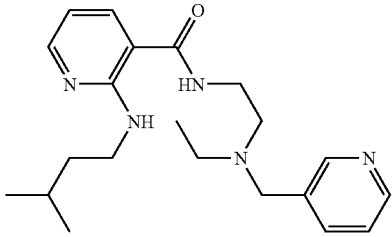 |
| 137 | | 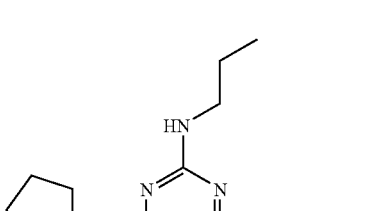 |

TABLE II

| NSI # | Chemical Descriptors LBB | % Prolif (Alamar) | Neuron Number (% of Control) | Neuron Ratio (% of Control) | % Neuron Ratio EC50/Eff | Neuron # EC50/Eff | Stauro % Inhib Neutron Number Nuclear Frag Caspase-3 | 2° Assay Cell #/Apop | Long Term Treatment Prolif/# Neur/ Neur Ratio |
|---|---|---|---|---|---|---|---|---|---|
| 106 | −1.1 CNS (−) | 211 ± 48 | 77 ± 12 | 92 ± 6 | 0.3 nM, $r^2$0.59 165% @ 100nM | 0.07 nM, $r^2$0.75 157% @ 300nM | 16 ± 19 N N | | 92 ± 3 137 ± 8 120 ± 5 |
| 127 | −1.0 CNS (−) | 181 ± 14 | 81 ± 13 | 104 ± 8 | 0.1 nM, $r^2$0.65 114% @ 10 nM | 1.5 nM, $r^2$0.5 137% @ 30000 nM | N N | | 103 ± 8 135 ± 21 |
| 130 | −1.5 CNS (−) | 92 ± 33 | 124 ± 8 | 128 ± 4 | 0.1 nM, $r^2$0.39 144% @ 30,000 nM | 2164 nM, $r^2$0.70 202% @ 10000 nM | N N 56 ± 17 | | 131 ± 15 115 ± 11 128 ± 30 |
| 142 | 0.1 CNS (++) | 115 ± 13 | 152 ± 22 | 125 ± 15 | 0.07 nM, $r^2$065 123% @ 30,000 nM | 0.001 nM, $r^2$0.70 175% @ 30000 nM | N N | | 92 ± 12 105 ± 26 146 ± 34 |
| 143 | 0.01 CNS (++) | 97 ± 16 | 143 ± 6 | 130 ± 14 | 445 nM, $r^2$0.82 112% @ 30000 nM | 4.8 nM, $r^2$0.62 115% @ 30000 nM | N 123 ± 77 | | 120 ± 21 153 ± 33 102 ± 14 |
| 144 | −0.8 CNS (−) | 149 ± 15 | 179 ± 29 | 137 ± 8 | 18.1 nM, $r^2$0.73 138% @ 300 nM | 13.5 nM, $r^2$0.96 186% @ 300 nM | N N N | | 103 ± 12 97 ± 21 170 ± 46 |
| 149 | −0.3 CNS (+) | 216 ± 28 | 113 ± 16 | 100 ± 6 | 333 nM, $r^2$0.75 111% @ 1000 nM | <0.1 nM, $r^2$0.66 124% @ 1000 nM | 47 ± 15 N | | 123 ± 12 89 ± 13 171 ± 19 |
| 150 | −0.2 CNS (+) | 177 ± 44 | 107 ± 29 | 99 ± 6 | <.01 nM, $r^2$0.77 112% @ 30000 nM | 85 nM, $r^2$0.90 227% @ 3000 nM | N | | 143 ± 11 110 ± 25 120 ± 10 |
| 157 | −0.8 CNS (−) | 218 ± 140 | 135 ± 15 | 142 ± 6 | >1000 nM, $r^2$0.67 146% @ 30000 nM Tox hi dose | >1000 nM, $r^2$0.75 113% @ 10000 nM Tox hi dose | N N N | | 105 ± 7 146 ± 19 139 ± 43 107 ± 22 |

TABLE II-continued

| NSI # | Chemical Descriptors LBB | % Prolif (Alamar) | Neuron Number (% of Control) | Neuron Ratio (% of Control) | % Neuron Ratio EC50/Eff | Neuron # EC50/Eff | Stauro % Inhib Neutron Number Nuclear Frag Caspase-3 | 2° Assay Cell #/Apop | Long Term Treatment Prolif/# Neur/ Neur Ratio |
|---|---|---|---|---|---|---|---|---|---|
| 158 | −0.5 CNS | 236 ± 79 | 93 ± 17 | 106 ± 9 | 36 nM, r²0.48 106% @ 3000 nM | 0.2 nM, r²0.88 145% @ 300 nM | 22 ± 18 N 48 ± 14 | | 99 ± 6 141 ± 24 114 ± 14 |
| 182 | −0.5 CNS | 74 ± 8 | 95 ± 9 | 125 ± 10 | 0.01 nM, r²0.54 112% @ 10000 nM | 0.1 nM, r²0.83 123% @ 300 nM | N 85 ± 45 108 ± 21 | N/N 78 ± 34/ 100 ± 27 | 95 ± 6 121 ± 13 111 ± 13 |
| 183 | −0.6 CNS | 69 ± 18 | 128 ± 13 | 131 ± 4 | No Curve 112% @ 1 nM | 0.05 nM, r²0.60 140% @ 300nM | N N N | N 40 ± 33 | 99 ± 19 148 ± 30 111 ± 16 |
| 185 | −1.3 CNS (−) | 73 ± 26 | 141 ± 70 | 135 ± 15 | >1000 nM, r²0.895 112% @ 30000nM | 786 nM, r²0.538 132% 3000 nM | 30 ± 19/ 13 ± 12 N/N | | 83 ± 25 155 ± 30 105 ± 19 |
| 189 | 0.3 CNS (++) | 70 ± 21 | 102 ± 41 | 130 ± 19 | 411 nM, r²0.82 141% @ 30000 nM | 253 nM, r²0.76 165% @ 30000 nM | N/N 121 ± 74/ 182 ± 39 | | 144 ± 17 110 ± 26 96 ± 19 |
| 190 | 0.1 CNS (++) | 76 ± 14 | 130 ± 22 | 127 ± 9 | >.001 nM, r²0.36 128% @ 1 nM | 13 nM, r²0.64 165% @ 300 nM | 42 ± 25/ 32 ± 1 42 ± 30/N | | 98 ± 11 121 ± 19 100 ± 12 |
| 137 | −0.85 CNS (−) | 108 ± 28 | 151 ± 40 | 116 ± 8 | >1000, r²0.77 126% @ 30000 nM | >1000 nM, r²0.75 145% @ 30000 nM | N 87 ± 41 N | | 111 ± 10 139 ± 35 98 ± 18 |

The invention is claimed as follows:

1. A composition comprising a neurogenic agent, said neurogenic agent including a nicotinamide having the structure selected from the group consisting of a)
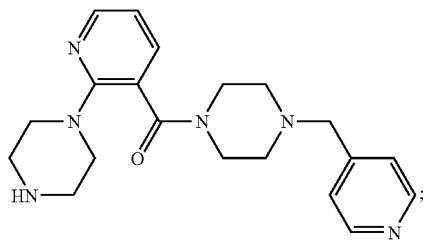

b)
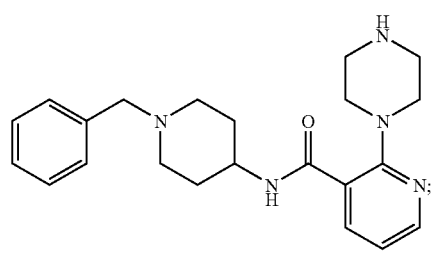

f)
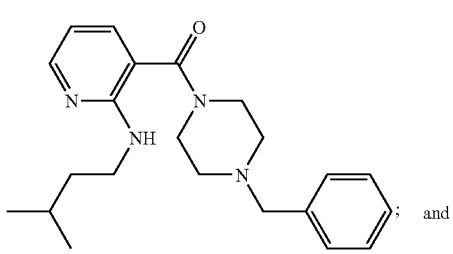

g)
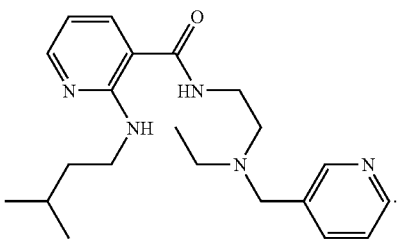

and

2. The composition of claim 1, wherein the nicotinamide has the structure b
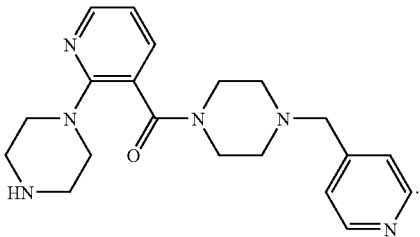

3. The composition of claim 1, wherein the nicotinamide has the structure b
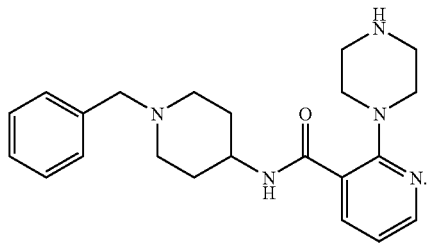

4. The composition of claim 1, wherein the nicotinamide has the structure
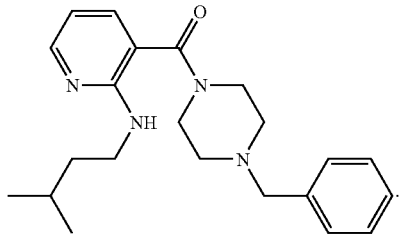
b)
5. The composition of claim 1, wherein the nicotinamide has the structure
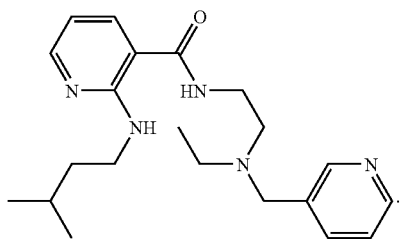
b)
6. A compound having the structure selected from the group consisting of
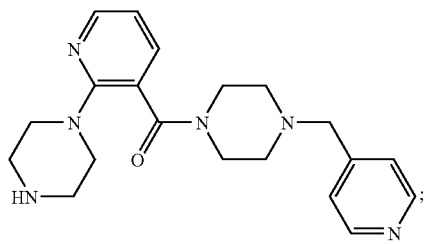
a)
-continued
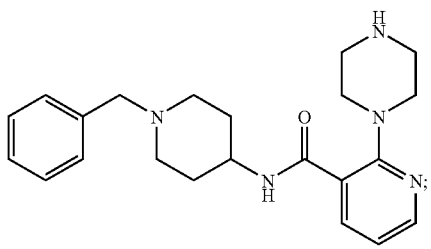
b)
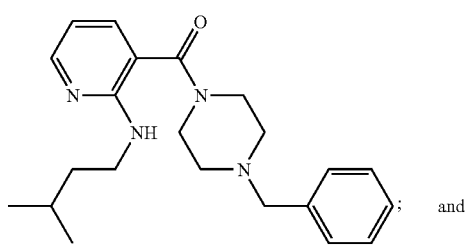
f)
; and
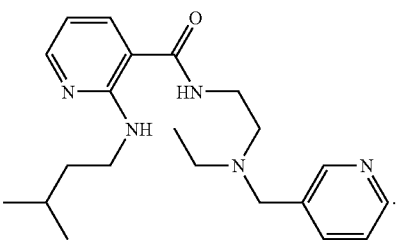
g)
7. The compound of claim 6, wherein said compound is included in a pharmaceutical composition.
* * * * *